(12) United States Patent
Mazzeo et al.

(10) Patent No.: US 11,684,686 B2
(45) Date of Patent: Jun. 27, 2023

(54) FLEXIBLE PLASMA APPLICATORS BASED ON FIBROUS LAYERS

(71) Applicants: Rutgers, The State University of New Jersey, New Brunswick, NJ (US); University of Florida Research Foundation, Incorporated, Gainesville, FL (US)

(72) Inventors: Aaron Mazzeo, New Brunswick, NJ (US); Jingjin Xie, Piscataway, NJ (US); Qiang Chen, Somerset, NJ (US); Subrata Roy, Gainesville, FL (US)

(73) Assignees: RUTGERS, THE STATE UNIVERSITY OF NEW JERSEY, New Brunswick, NJ (US); UNIVERSITY OF FLORIDA RESEARCH FOUNDATION, INCORPORATEDg, Gainesville, FL (US)

( * ) Notice: Subject to any disclaimer, the term of this patent is extended or adjusted under 35 U.S.C. 154(b) by 426 days.

(21) Appl. No.: 16/853,983

(22) Filed: Apr. 21, 2020

(65) Prior Publication Data
US 2020/0246496 A1 Aug. 6, 2020

Related U.S. Application Data

(63) Continuation-in-part of application No. 15/425,474, filed on Feb. 6, 2017, now Pat. No. 10,646,604.
(Continued)

(51) Int. Cl.
*A61L 2/14* (2006.01)
*A61L 9/22* (2006.01)
(Continued)

(52) U.S. Cl.
CPC .............. *A61L 2/14* (2013.01); *A23L 3/26* (2013.01); *A23L 3/3445* (2013.01); *A23L 3/34095* (2013.01); *A61L 2/0011* (2013.01); *A61L 2/0094* (2013.01); *A61L 2/202* (2013.01); *A61L 2/26* (2013.01); *A61L 9/046* (2013.01); *A61L 9/12* (2013.01); *A61L 9/22* (2013.01); *A61L 15/18* (2013.01); *B32B 3/266* (2013.01);
(Continued)

(58) Field of Classification Search
CPC ....................................................... A61L 2/14
See application file for complete search history.

(56) References Cited

U.S. PATENT DOCUMENTS

| 8,564,558 | B2 | 10/2013 | Yi et al. | |
|---|---|---|---|---|
| 10,646,604 | B2 * | 5/2020 | Mazzeo | ............. A61L 2/14 |

(Continued)

FOREIGN PATENT DOCUMENTS

| CN | 201805613 | * | 4/2011 |
| CN | 201805613 U | | 4/2011 |

OTHER PUBLICATIONS

Yu et al. CN 201805613. Apr. 2011. English machine translation. (Year: 2011).*
(Continued)

*Primary Examiner* — Donald R Spamer
(74) *Attorney, Agent, or Firm* — Fox Rothschild LLP

(57) ABSTRACT

Disclosed herein are flexible plasma applicators based on fibrous layers that are capable of rapidly sanitizing a surface via either direct or indirect contact with said surface.

17 Claims, 13 Drawing Sheets

Related U.S. Application Data

(60) Provisional application No. 62/291,082, filed on Feb. 4, 2016.

(51) Int. Cl.

| | | |
|---|---|---|
| *A61L 9/04* | (2006.01) | |
| *A61L 9/12* | (2006.01) | |
| *A61L 2/20* | (2006.01) | |
| *A61L 2/26* | (2006.01) | |
| *A61L 2/00* | (2006.01) | |
| *C01B 13/11* | (2006.01) | |
| *A61L 15/18* | (2006.01) | |
| *A23L 3/26* | (2006.01) | |
| *A23L 3/3409* | (2006.01) | |
| *A23L 3/3445* | (2006.01) | |
| *B32B 3/26* | (2006.01) | |
| *B32B 29/00* | (2006.01) | |
| *B32B 7/12* | (2006.01) | |
| *G01N 33/00* | (2006.01) | |
| *H05H 1/24* | (2006.01) | |

(52) U.S. Cl.
CPC .............. *B32B 7/12* (2013.01); *B32B 29/005* (2013.01); *C01B 13/115* (2013.01); *G01N 33/0027* (2013.01); *H05H 1/2439* (2021.05); *A23V 2002/00* (2013.01); *A61L 2202/11* (2013.01); *A61L 2202/24* (2013.01); *A61L 2202/26* (2013.01); *A61L 2209/212* (2013.01); *B32B 2255/12* (2013.01); *B32B 2255/205* (2013.01); *B32B 2255/26* (2013.01); *B32B 2255/28* (2013.01); *B32B 2307/202* (2013.01); *B32B 2307/204* (2013.01); *B32B 2437/02* (2013.01); *B32B 2457/208* (2013.01); *B32B 2535/00* (2013.01); *C01B 2201/12* (2013.01); *H05H 1/2418* (2021.05)

(56) References Cited

U.S. PATENT DOCUMENTS

| | | | |
|---|---|---|---|
| 2004/0223882 A1* | 11/2004 | Bonne | G01N 1/24 422/82.11 |
| 2010/0296977 A1 | 11/2010 | Hancock | |
| 2011/0116967 A1* | 5/2011 | Roy | H05H 1/2406 422/186.05 |
| 2014/0186525 A1 | 7/2014 | Seong et al. | |
| 2017/0136252 A1* | 5/2017 | Weltmann | A61L 2/14 |
| 2017/0224856 A1* | 8/2017 | Mazzeo | H05H 1/2406 |

OTHER PUBLICATIONS

Mazzeo, et al: "Paper-Based, Capacitive Touch Pads", Advanced Materials, 2012, vol. 24, No. 21, pp. 2850-2856.

* cited by examiner

FLEXIBLE PLASMA APPLICATORS BASED ON FIBROUS LAYERS

CROSS-REFERENCE TO RELATED APPLICATIONS

The present application is a continuation-in-part of U.S. patent application Ser. No. 15/425,474, filed Feb. 6, 2017, which claims priority under 35 U.S.C. § 119(e) to provisional application No. 62/291,082, filed on Feb. 4, 2016. The entire disclosures of the application noted above are incorporated herein by reference in their entireties.

FIELD OF THE INVENTION

This disclosure relates generally to a flexible plasma applicator and the applications thereof.

BACKGROUND OF THE INVENTION

Healthcare-associated infections (HAIs), also referred to as nosocomial infections, are among the most significant cause of morbidity and mortality in healthcare settings, such as in hospitals, throughout the developed and developing world. At any given time, approximately 7% of hospitalized patients in developed countries, and about 10% of those hospitalized patients in developing countries, will acquire at least one HAI. For example, in 2011, in the United States, approximately 721,800 HAIs were reported in hospitals. Of those, approximately 721,800 reported HAIs, approximately 75,000 of those patients died during their hospitalization. Put differently, over approximately 10% of those individuals who were diagnosed with at least one HAI in 2011 in the US died during hospitalization. Furthermore, international public health crises, such as the 2014 West African Ebola virus outbreak, and the rapidly growing number of antibiotic-resistant bacteria, including multi-drug resistant and extensively-drug resistant bacteria, represent a significant area of public health concern worth addressing in a cost-effective manner.

Existing plasma generators are typically capable of sanitizing medical devices and killing microbes in atmospheric conditions. However, these plasma-based generators use rigid components which are not capable of bending or conforming to irregularly shaped objects. This lack of flexibility limits potential use and applications. Furthermore, existing plasma generators are expensive and not ecologically friendly for single use in contaminated or sterile environments. Accordingly, there is a need for flexible, economical plasma-based applicators.

SUMMARY OF THE INVENTION

This disclosure addresses the need mentioned above in a number of aspects. In one aspect, this disclosure provides a plasma applicator comprising: a first substrate layer, a second substrate layer, an adhesive layer, and optionally a polymer coating layer. The first substrate layer and the second substrate layer are comprised of a fibrous base layer and a metallic surface layer. The adhesive layer binds the fibrous base layer of the first substrate layer to the fibrous base layer of the second substrate layer. The polymer coating layer is applied to the metallic surface layer of at least one of the first substrate layer and the second substrate layer. The metallic surface layer of the first substrate layer and the metallic surface layer of the second substrate are exposed and configured to be placed in conductive contact with a high voltage source to generate dielectric barrier discharge (DBD)-based plasma comprising at least one of volume plasma and surface plasma upon exposure to the high voltage source. In some embodiments, the DBD-based plasma comprises both volume plasma and surface plasma.

In some embodiments, the plasma applicator comprises at least one polymer layer inserted between at least one of (i) the fibrous base layer and the metallic surface layer of the first substrate layer and (ii) the fibrous base layer and the metallic surface layer of the second substrate layer.

In some embodiments, the plasma applicator comprises a conductive polymer coating layer applied to the exposed metallic surface layer of at least one of the first substrate layer and the second substrate layer.

In some embodiments, the DBD-based plasma is configured to generate ozone. In some embodiments, the DBD-based plasma is configured to kill or inhibit growth of a microorganism or a virus on a surface or on an object.

In some embodiments, the high voltage source is configured to apply an alternating current (AC) input with a frequency of about 1 kHz to about 10 kHz to the plasma applicator. In some embodiments, the AC input has a peak-to-peak voltage (Vp-p) ranging from about ±0.5 kV to about ±5 kV. In some embodiments, the AC input has a voltage of about 1 kV to about 100 kV.

In some embodiments, the plasma applicator comprises a power source to generate plasma. In some embodiments, the AC input applied to the plasma applicator has a voltage of about 1 kV to about 100 kV and a frequency greater than 1 kHz.

In some embodiments, the substrate layer is patterned. In some embodiments, the first substrate layer comprises a plurality of hexagon-shaped apertures that form a honeycomb pattern. In some embodiments, the plasma applicator has a substantially circular shape.

In another aspect, the plasma applicator, as disclosed, can be incorporated into various devices or articles. In one example, this disclosure provides a bandage (e.g., a flexible bandage) for promoting wound healing that comprises the plasma applicator described above and a non-conductive spacer attached on a surface of the plasma applicator, the non-conductive spacer being adapted to be placed on skin tissue.

In another example, this disclosure also provides a device (e.g., a handheld device) comprising the plasma applicator for disinfecting or sanitizing an object. In some embodiments, the plasma applicator can be a disposable or replaceable plasma applicator insert. In some embodiments, the object comprises food or produce. In some embodiments, the device can be a packaging container.

In another example, this disclosure additionally provides a self-sanitizing article comprising the plasma applicator. In some embodiments, the article comprises a device controlling interface, such as a touchpad (e.g., a capacitive touchpad), a button, a knob, a dial, a switch, a touchscreen, a key, a keyboard or the like. In some embodiments, the device controlling interface is based on capacitive technologies. In some embodiments, the article comprises a wheel.

In another example, this disclosure further provides a system comprising the plasma applicator described above for deodorizing an object. In some embodiments, the object comprises an article of footwear or a fabric product.

In yet another example, this disclosure also provides a device comprising the plasma applicator for oxidizing an article. In some embodiments, the article is a gas sensor, wherein the DBD-based plasma is configured to oxidize the sensor and thereby to reset the gas sensor.

In another aspect, this disclosure provides a method of disinfecting or sanitizing a surface using a plasma applicator. The method comprises (i) placing a plasma applicator over the surface and thereby to cause the plasma applicator to directly contact the surface or to maintain a predetermined distance over the surface; and (2) applying an AC input from the high voltage source and keeping the plasma applicator over the surface for a predetermined amount of time, thereby causing the plasma applicator to generate DBD-based plasma that kills or inhibits growth of a microorganism or a virus on the surface. The plasma applicator comprises: a first substrate layer, a second substrate layer, an adhesive layer, and optionally a polymer coating layer. The first substrate layer and the second substrate layer are comprised of a fibrous base layer and a to metallic surface layer. The adhesive layer binds the fibrous base layer of the first substrate layer to the fibrous base layer of the second substrate layer. The polymer coating layer is applied to the metallic surface layer of at least one of the first substrate layer and the second substrate layer. The metallic surface layer of the first substrate layer and the metallic surface layer of the second substrate are exposed and configured to be placed in conductive contact with a high voltage source to generate DBD-based plasma comprising at least one of volume plasma and surface plasma upon exposure to the high voltage source. In some embodiments, the DBD-based plasma comprises both volume plasma and surface plasma.

In some embodiments, the surface is a surface of skin tissue, a surface of food or produce, a surface of an object or a device interface. In some embodiments, the object comprises a wheel or a medical device. In some embodiments, the object comprises personal protective equipment (PPE), e.g., a face mask. In some embodiments, the device interface comprises a touchpad, a button, a knob, a dial, a switch, a touchscreen, a key, or a keyboard.

In some embodiments, the predetermined distance is between about 0.1 cm and about 10 cm. In some embodiments, the step of applying comprises applying the AC input with a frequency of about 1 kHz to about 10 kHz to the plasma applicator. In some embodiments, the step of applying comprises applying the AC input with a frequency of about 1.0 kHz to about 3.5 kHz to the plasma applicator. In some embodiments, the AC input has a peak-to-peak voltage (Vp-p) ranging from about ±0.5 kV to about ±5 kV. In some embodiments, the AC input has a peak-to-peak voltage (Vp-p) ranging from about ±2.0 kV to about ±3.5 kV. In some embodiments, the step of applying comprises applying the AC input with a voltage of about 1 kV to about 100 kV to the plasma applicator. In some embodiments, the predetermined amount of time is between about 5 seconds and about 5 minutes.

In another aspect, this disclosure also provides a method of deodorizing an article using a plasma applicator. The method comprises (a) placing a plasma applicator over a surface of the article and thereby to cause the plasma applicator to directly contact the surface or to maintain a predetermined distance over the surface; and (b) applying an AC input from the high voltage source and keeping the plasma applicator over the surface for a predetermined amount of time, thereby causing the plasma applicator to generate DBD-based plasma that reduces odor from the article. The plasma applicator comprises: a first substrate layer, a second substrate layer, an adhesive layer, and optionally a polymer coating layer. The first substrate layer and the second substrate layer are comprised of a fibrous base layer and a metallic surface layer. The adhesive layer binds the fibrous base layer of the first substrate layer to the fibrous base layer of the second substrate layer. The polymer coating layer is applied to the metallic surface layer of at least one of the first substrate layer and the second substrate layer. The metallic surface layer of the first substrate layer and the metallic surface layer of the second substrate are exposed and configured to be placed in conductive contact with a high voltage source to generate DBD-based plasma comprising at least one of volume plasma and surface plasma upon exposure to the high voltage source. In some embodiments, the DBD-based plasma comprises both volume plasma and surface plasma.

In some embodiments, the step of applying comprises applying to the plasma applicator the AC input with a frequency of about 1.0 kHz to about 3.5 kHz and a peak-to-peak voltage (Vp-p) ranging from about ±2.0 kV to about ±3.5 kV. In some embodiments, the predetermined amount of time is between about 5 seconds and about 5 minutes. In some embodiments, the method results in near-complete disinfection within 120 seconds, within 60 seconds, with 30 seconds, within 20 seconds, within 10 seconds, or within 5 seconds.

In some embodiments, the article comprises an article of footwear or a fabric product selected from the group consisting of shoe insole, clothes, pillow, pillow cover, bed cover, blanket, table cloth, carpet, and curtain.

In yet another aspect, this disclosure further provides a method of oxidizing an object. The method comprises (i) placing the plasma applicator described above over a surface of the article and thereby to cause the plasma applicator to directly contact the surface or to maintain a predetermined distance over the surface; and (2) applying an AC input from the high voltage source and keeping the plasma applicator over the surface for a predetermined amount of time, thereby causing the plasma applicator to generate DBD-based plasma that oxidizes the article.

In some embodiments, the article is a gas sensor, wherein the DBD-based plasma is configured to oxidize the sensor and thereby to reset the gas sensor.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DESCRIPTION OF THE DRAWINGS

FIGS. 16A and 16B are a set of graphs showing pH value of baby spinach leaves (FIG. 16A) or whole tomatoes (FIG. 16B) of various treatment time by SDBD plasma at the end of storage period (7 days). Mean±SD. Means followed by the same letter in the same column are non-significant at $P<0.05$ according to Tukey's HSD test.

DETAILED DESCRIPTION OF THE INVENTION

A. Healthcare-Associated Infections/Nosocomial Infections

There are numerous potential underlying causes for HAIs. However, a significant number of HAIs are directly attributable to improper or insufficient sanitation and/or disinfection practices in healthcare settings, such as in a hospital. According to the World Health Organization (WHO), an estimated 40% of HAIs are caused by poor hand hygiene. This may result in cross-contamination and spread of infectious agents, including both pathogenic agents such as E. coli and opportunistic agents, such as fungus or yeast, or opportunistic bacteria such as Clostridium difficile (C. difficile). Many HAIs are caused by drug-resistant bacteria, i.e., methicillin-resistant Staphylococcus aureus (MRSA) and vancomycin-resistant enterococci (VRE). A significant number of bacterial HAIs are Gram-negative bacteria, and a significant number of Gram-negative bacterial infections are antibiotic-resistant. Gram-negative bacterial infections that are common in hospital settings include bacterial pneumonia, bloodstream infections, wound or surgical site infections, and bacterial meningitis. In general, invasive surgery carries a much higher risk than non-invasive surgical procedures in acquiring HAIs.

B. Plasma Applicators i. Plasma Sanitation

"Plasma" is defined herein as the fundamental state of matter characterized by a quasi-neutral collection of electrons, positive ions, and neutrals capable of collective behavior. Plasma is further characterized by a lack of molecular bonds. The presence of a significant number of charge carriers renders plasma electrically conductive so that it responds strongly to magnetic fields. Plasma does not have a definite shape or volume, like gasses. However, unlike gases, plasma may form structures such as filaments, beams, and layers under the influence of a magnetic field. Sanitation by plasma discharge generally occurs through three synergistic mechanisms: free radical interactions, UV/VUV radiative effects, and volatilization.

ii. Plasma Applicator Structure and Construction

The plasma applicators of the present invention utilize dielectric barrier discharge (DBD) technology that allows for plasma discharge to reach material surface. DBD is defined herein as is the gas-discharge between two electrodes, separated by one or more dielectric layers and a gas-filled gap. The plasma applicators of the present invention operate at atmospheric pressure, room temperature, at an alternating current (AC) voltage of about 1 kV to about 100 kV, and a frequency greater than 1 kHz, for example from about 2 kHz to about 10 kHz, although no set frequency is required over 1 kHz.

Figure 1:
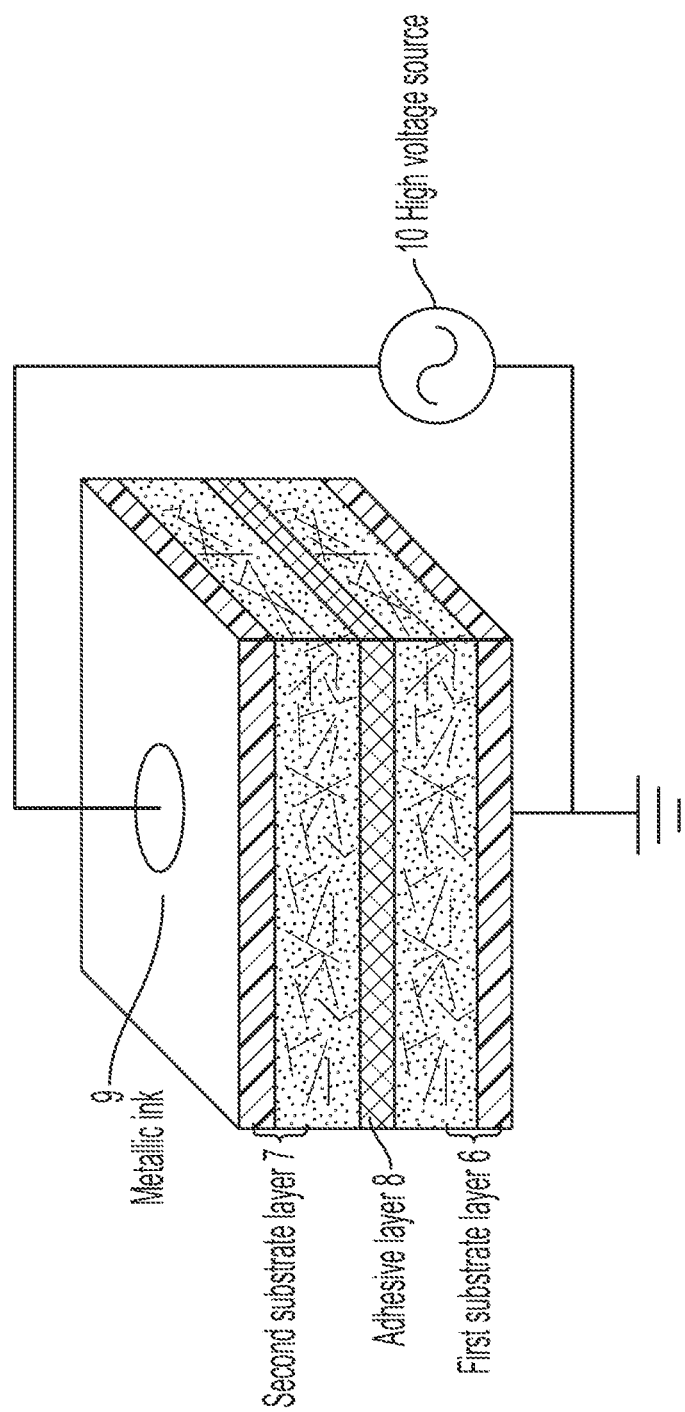
FIG. 1 represents an exemplary plasma applicator utilizing dielectric barrier discharge (DBD) technology of the present invention.
Figure 2:
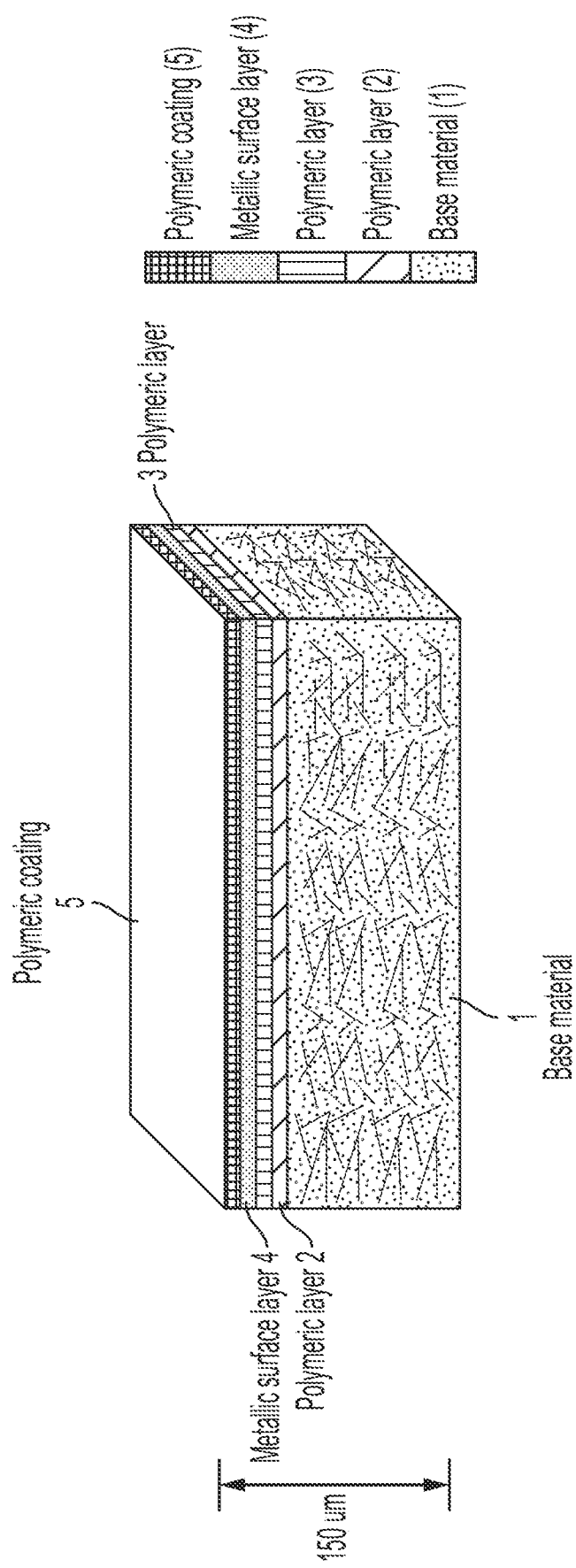
FIG. 2 represents an exemplary structure of the substrate layers, with optional interior polymeric layers and optional polymeric coating represented.

The plasma applicators are organized in a "two-layer" configuration, comprising a first substrate layer 6, a second substrate layer 7, and an interior adhesive layer 8 that binds the first substrate to the second substrate layer (FIG. 1). The thickness of the substrate layers 6, 7 may be variable, but optimally are around 150 μm in thickness (FIG. 2). The thickness of the adhesive layer may be variable, but optimally is around 30 μm in thickness. The substrate layers may be thicker or thinner, so long as the electric potential across the two electrodes remains high enough to induce dielectric discharge and so long as the high electrical potential below the dielectric strength of the substrate. The overall thickness of the plasma applicators may be up to about 2 mm in thickness, with each substrate layer 6, 7 being up to about 1 mm. The substrate layers are comprised of a base material comprising fibrous material. The fibrous material may be either natural fibrous material or synthetic fibrous material, e.g., rayon or woven synthetic polyester. Natural fibrous material as defined herein includes any base material derived from natural sources, including but not limited to both woven and non-woven fiber substrates, e.g., non-woven cellulosic fiber substrates such as paper, pressed pulp, and other related materials, and other materials such as a scrim or scrim layer, leather, or textiles. Cellulose-based paper is of particular interest as a base material, as it is a flexible, renewable, and biodegradable material. Cellulose-based paper has tunable porosity to allow gases to permeate its bulk volume and is capable of handling temperatures of up to 250° C. These properties make cellulose-based paper suitable as a base material for the plasma applicators of the present invention as the permeability of cellulose-based paper allows the flow of gas through the substrate to provide fuel for the plasma and to cool the cellulose-based paper with forced convection. Accordingly, in some embodiments, the base material for the first substrate layer and/or the second substrate layer of the plasma applicators of the present invention comprises cellulose-based paper.

The first substrate layer 6 and the second substrate layer 7 are assembled as follows (FIG. 2). Optionally, at least one polymeric layer 2, 3 is layered on top of the base material 1, followed by a metallic surface layer 4, and optional polymeric coating 5. The optional at least one polymeric layer(s) 2, 3 are preferably non-conductive and serve to ensure the stability of the overall plasma applicator. The optional polymeric coating 5 serves a similar purpose, in providing improved structural stability and likewise is preferably non-conductive.

Preferably, the metallic surface layer 4 is comprised of vacuum evaporated aluminum, but any conductive metal is appropriate. The first 6 and second 7 substrate layers are oriented in the plasma applicators such that the adhesive layer 8 binds to the base material 1 of each to substrate layer 6, 7, thus exposing the metallic surface layers 4 (or the optional polymeric coating 5) on the outer surfaces of the plasma applicators. The metallic surface layers 4 (with optional polymeric coating 5) serve as electrodes, while the base material 1 and adhesive layer 8 serve as an insulating dielectric barrier. Optionally, a conductive layer of metallic ink 9, e.g., conductive silver ink, or other similar substance is placed on the contact points of the exposed metallic surface layers 4 (or optional polymeric coating 5) of the plasma applicator. The plasma applicator may further comprise an additional porous insulation layer between the first substrate layer 6 and the second substrate layer 7, which may render the plasma applicator especially suitable for use as a bandage for skin treatment. A bandage for skin treatment may additionally comprise a non-conductive spacer placed on an exposed surface of either the first substrate layer 6 or on an exposed surface of the second substrate layer 7, whichever layer would be coming in contact with the skin. The non-conductive spacer may be thermally insulating, and may be electrically insulating. The plasma applicators of the present invention are capable of generating both surface plasma and volume plasma.

Figure 3:
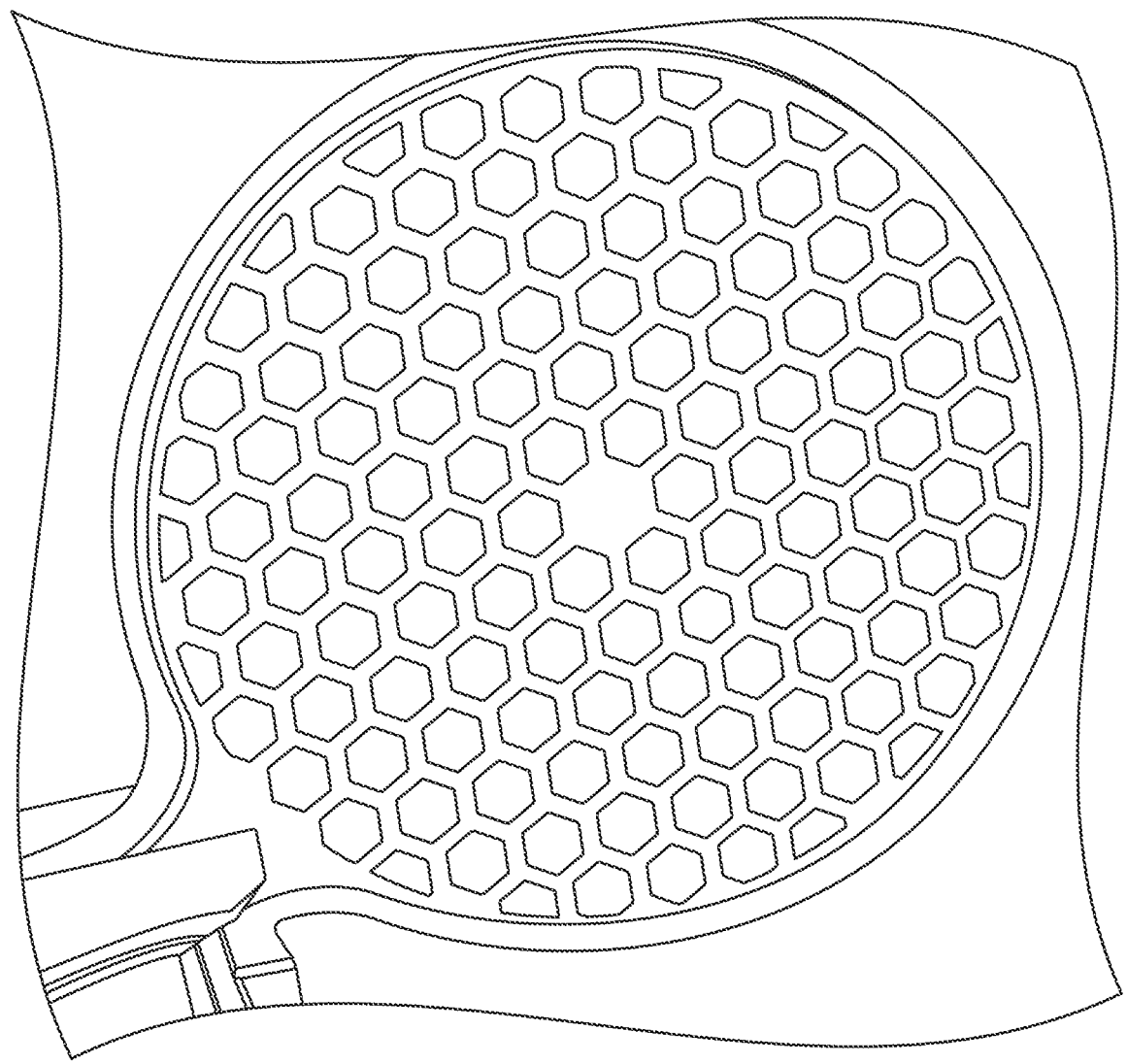
FIG. 3 represents an exemplary structure of a plasma applicator in a circular configuration and portraying an optional "honeycomb" design.

One or both of the metallic surface layers 4 of the substrate layer(s) 6, 7 may be patterned, for example, on one or both of the surface(s) of the metallic surface layer(s) 4. Additionally, one or both of the substrate layer(s) 6, 7 may be patterned such that the exposed metallic surface layers are fabricated to on an overall shape or design, for example, but not necessarily a "honeycomb" design, thus partially exposing the base material 1 where the metallic surface layer 4 is cut away (FIG. 3). The patterning may be achieved, e.g., by laser etching and/or laser engraving, by mechanical means, such as by hole punching, or by chemical reaction, e.g., with acid. The goal of such patterning may be to increase airflow, which can lead to an increased generation of plasma, including surface plasma and volume plasma.

To generate both surface and volume plasma, a high voltage source 10 is applied to the contact points on the surfaces of the DBD. For example, to produce plasma, the present invention utilized sinusoidal signals with frequencies ranging from about 1 kHz to about 8 kHz and peak-to-peak voltages $V_{p-p}$ ranging from about ±0.5 V to about ±5 V using a function generator (4011A, BK Precision). This signal was amplified using a high-voltage amplifier (Model 10/10, TREK) with a gain of 1000 to output a high oscillating potential $V_{p-p}$ ranging from ±500 V to ±5 kV. The generation of plasma was frequency-dependent. While not wishing to be bound by theory, this suggests the existence of an optimal frequency at a given electrical potential to generate uniform coverage of plasma.

Figure 4:
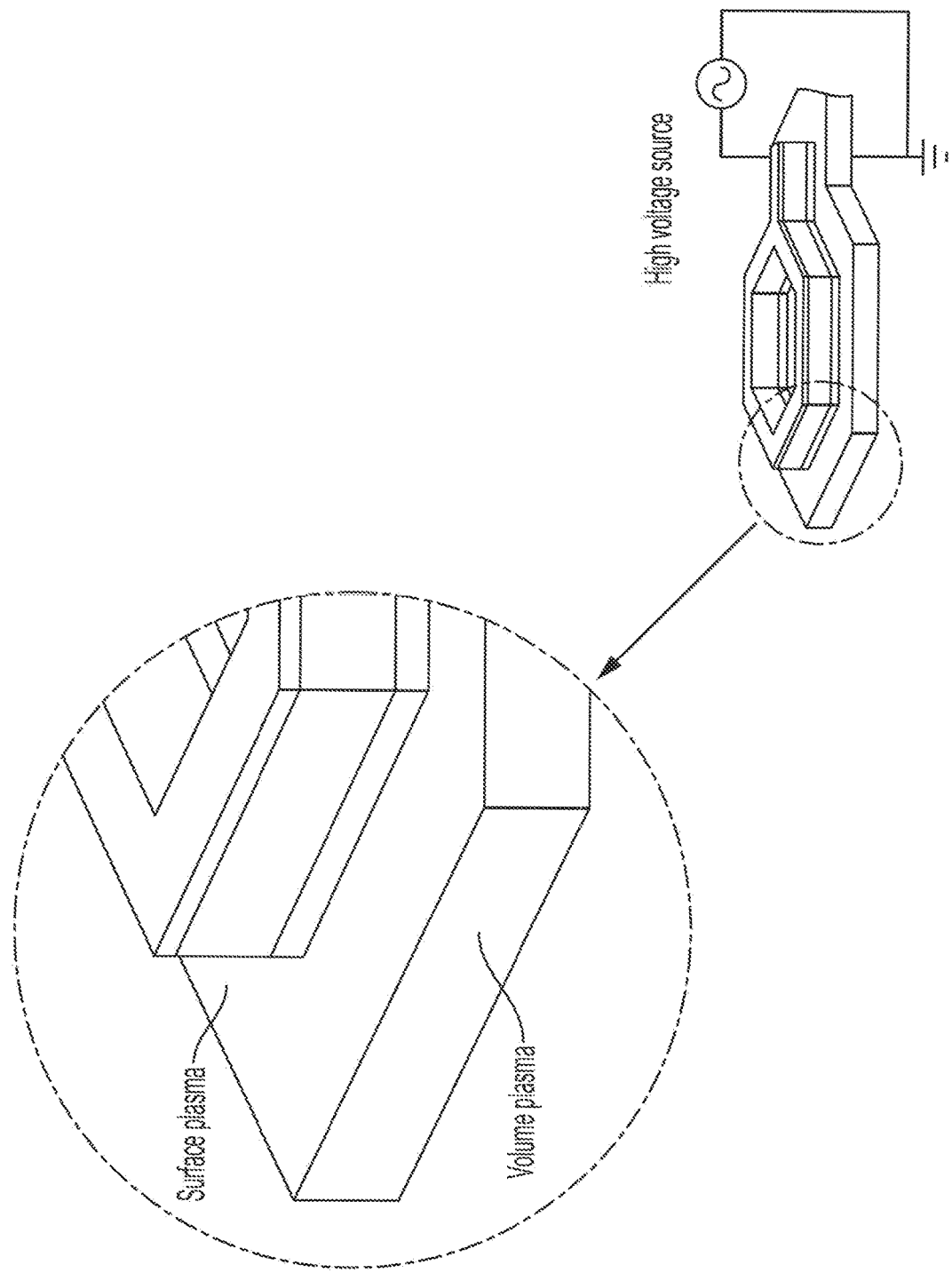
FIG. 4 represents the typical geometry and location of both volume plasma and surface plasma in a plasma applicator.

Generally, DBD can produce two types of plasma, volume plasma and surface plasma, depending on the configuration of the DBD. In each instance, the DBD is comprised of one or more dielectric insulators sandwiched by electrodes. However, volume plasma is ordinarily generated when there is a discharge gap between the two electrodes that is large enough to contain an adequate amount of air. In some circumstances where the discharge gap is major, volume plasma is the primary discharge, i.e., the major discharge is between the two electrodes. If, however, the gap between the electrodes is very small or non-existent, surface plasma is generated as the discharge will occur on the surfaces around the electrodes. The typical geometry and location of both volume plasma and surface plasma is illustrated in FIG. 4.

Surprisingly, however, the present invention may be capable of generating both surface and volume plasma, a distinct advantage that directly arises from the use of fibrous base material. Such base material may be naturally porous, especially in the case of natural fibrous material, opposed to non-porous polymer base materials, and such porous materials may allow for an adequate amount of air to fill in small gaps between the two electrodes to generate volume plasma in addition to surface plasma that is generated. The capability of generating both surface and volume plasma gives rise to the ability to sanitize not only the objects closed to a sanitizer via surface plasma, but also the plasma applicator itself via volume plasma. The raw material comprising the base layer, for example, but not limited to cellulose-based paper, may contain microbes inside its porous, fibrous structure. With the presence of volume plasma, it is possible to deactivate these residing microbes.

According to one aspect of this disclosure, the plasma applicator comprises: a first substrate layer, a second substrate layer, an adhesive layer, and optionally a polymer coating layer. The first substrate layer and the second substrate layer are comprised of a fibrous base layer and a metallic surface layer. The adhesive layer binds the fibrous base layer of the first substrate layer to the fibrous base layer of the second substrate layer. The polymer coating layer is applied to the metallic surface layer of at least one of the first substrate layer and the second substrate layer. The metallic surface layer of the first substrate layer and the metallic surface layer of the second substrate are exposed and configured to be placed in conductive contact with a high voltage source to generate DBD-based plasma comprising at least one of volume plasma and surface plasma upon exposure to the high voltage source. In some embodiments, the DBD-based plasma comprises both volume plasma and surface plasma.

In some embodiments, the plasma applicator comprises at least one polymer layer inserted between at least one of (i) the fibrous base layer and the metallic surface layer of the first substrate layer and (ii) the fibrous base layer and the metallic surface layer of the second substrate layer.

In some embodiments, the plasma applicator comprises a conductive polymer coating layer applied to the exposed metallic surface layer of at least one of the first substrate layer and the second substrate layer.

In some embodiments, the DBD-based plasma is configured to generate ozone. In some embodiments, the DBD-based plasma is configured to kill or inhibit growth of a microorganism or a virus on a surface or on an object.

In some embodiments, the high voltage source is configured to apply an AC input with a frequency of about 1 kHz to about 10 kHz (e.g., about 1.0 kHz to about 3.5 kHz, about 1.2 kHz to about 1.5 kHz) to the plasma applicator. In some embodiments, the AC input has a peak-to-peak voltage (Vp-p) ranging from about ±0.5 kV to about ±8.5 kV (e.g., about ±0.5 kV to about ±5 kV, about ±2.0 kV to about ±3.5 kV). In some embodiments, the AC input has a voltage of about 1 kV to about 100 kV.

In some embodiments, the plasma applicator comprises a power source to generate plasma. In some embodiments, the AC input applied to the plasma applicator has a voltage of about 1 kV to about 100 kV and a frequency greater than 1 kHz.

In some embodiments, the substrate layer is patterned. In some embodiments, the first substrate layer comprises a plurality of hexagon-shaped apertures that form a honeycomb pattern. In some embodiments, the plasma applicator has a substantially circular shape.

iii. Advantages/Methods of Use

The plasma applicators of the present invention have a number of advantages, both technical and economical, over the current devices and methods, including preventing HAIs. Low-cost plasma applicators using, for example, cellulose-based paper as a base material, may reduce the rate of morbidity and mortality resulting from nosocomial infections in healthcare facilities. However, the use of the plasma applicators of the present invention is not limited to such use. The field of uses for the plasma applicators of the present invention is broad and may be applied in any circumstance in which disinfection is desired. For example, the plasma applicators of the present invention may be used to disinfect surfaces, sanitize food during food processing, and be applied to a wound for treatment, for example, but not necessarily as a bandage or wound dressing. The plasma applicators may also be utilized to disinfect electronic equipment. In particular, the plasma applicators of the present invention are well-suited for chronic or non-healing wounds that are susceptible to infection, e.g., ulcers, including venous and arterial ulcers, diabetic ulcers, and pressure ulcers, or for other openings, such as stomas.

The plasma applicators of the present invention may be especially well-suited for those individuals who are immunocompromised. The plasma applicators of the present invention may also be utilized with capacitive touch-technology to create self-sanitizing touchpads.

The plasma applicators of the present invention may be utilized to disinfect either via direct contact with a surface or indirect contact with a surface. Direct contact with a surface may be utilized, for example, in a wound dressing or bandage, or may be used in other settings such as sanitation of equipment. Indirect contact may have a number of uses, including passing objects through a volume or space in which plasma is being generated for sanitation and/or preservation purposes, such as foodstuffs or equipment, or for any other surface or object in which direct contact would be undesirable. Non-contact or indirect contact may occur at a distance from about 0.5 cm to about 1.0 cm from the surface to be sanitized, although distances as close to about 0 mm and as far as about 3 cm from the surface would be acceptable.

The plasma applicators of the present invention effect surprisingly rapid surface sanitation—sanitation is seen within seconds in many circumstances. The plasma applicators of the present invention may achieve near-complete surface sanitation via direct contact in as little as 5 seconds in certain circumstances, and no more than 60 seconds. For indirect contact, the plasma applicators of the present invention may achieve near-complete surface sanitation in as little as 10 seconds and no more than 60 seconds.

The plasma applicators of the present invention are environmentally friendly. They are disposable and bio-degradable as the base material is made from fibrous material (e.g., cellulose-based paper) rather than the non-fibrous polymer-based dielectric materials found in other devices. Because the base material is made from fibrous material, and because the thickness of the substrate layers is limited to a size range of about 100 μm to about 2 mm, the plasma applicators of the present invention are non-rigid and flexible, meaning that they can be arranged in a wide number of shapes, contoured to a wide range of surfaces, and adapted to a wide range of utilities. Particularly for natural fibrous materials, especially cellulose-based paper, the plasma applicators may represent a significantly more economical solution than those employing more expensive synthetic polymer-based dielectric materials, yet exhibit the same or enhanced disinfectant capacity.

The plasma applicators of the present invention may come in variable shapes and size that can be suited to any particular need, as opposed to a fixed size, and may be portable, i.e., handheld, plasma-based bandages. This is because the plasma applicators of the present invention are designed from lightweight, thin, and flexible adhered substrate layers. Related to this, the fabrication process of the plasma applicators of the present invention is scalable. The plasma applicators of the present invention are customizable in shape, size, material, and width. Due to the relatively simple construction of the plasma applicators, the plasma applicators of the present invention represent economical and affordable solutions for disease control, inside hospital settings and outside of such, i.e., for treatment of food-borne infections, or for application in wound treatment. The plasma applicators of the present invention are non-corrosive. They do not contain bleach, alcohols, or other harsh chemical oxidizers or disinfectants, and do not rely on ethylene oxide. The plasma applicators of the present invention do not rely on potentially dangerous gamma radiation for disinfection, nor do they rely on electron beam sanitation employed by large, costly medical equipment.

The plasma applicators of the present invention are scalable. Notably, electrical resistance scaled with the size of the plasma applicators, consistent with previously reported methods of decreasing the frequency of applied voltage to generate plasma through resistive barrier discharge. For example, the frequency of excitation for a plasma applicator of 400 mm×276 mm was 100 Hz at a voltage $V_{p-p}$ of ±3 kV.

In another aspect, this disclosure provides a method of disinfecting or sanitizing a surface using a plasma applicator. The method comprises (i) placing a plasma applicator over the surface and thereby to cause the plasma applicator to directly contact the surface or to maintain a predetermined distance over the surface; and (2) applying an AC input from the high voltage source and keeping the plasma applicator over the surface for a predetermined amount of time, thereby causing the plasma applicator to generate DBD-based plasma that kills or inhibits growth of a microorganism or a virus on the surface. The plasma applicator comprises: a first substrate layer, a second substrate layer, an adhesive layer, and optionally a polymer coating layer. The first substrate layer and the second substrate layer are comprised of a fibrous base layer and a metallic surface layer. The adhesive layer binds the fibrous base layer of the first substrate layer to the fibrous base layer of the second substrate layer. The polymer coating layer is applied to the metallic surface layer of at least one of the first substrate layer and the second substrate layer. The metallic surface layer of the first substrate layer and the metallic surface layer of the second substrate are exposed and configured to be placed in conductive contact with a high voltage source to generate DBD-based plasma comprising at least one of volume plasma and surface plasma upon exposure to the high voltage source. In some embodiments, the DBD-based plasma comprises both volume plasma and surface plasma.

In some embodiments, the step of applying comprises applying to the plasma applicator the AC input with a frequency of about 1.0 kHz to about 3.5 kHz and a peak-to-peak voltage (Vp-p) ranging from about ±2.0 kV to about ±3.5 kV.

In some embodiments, the predetermined amount of time is between about 5 seconds and about 5 minutes. In some embodiments, the method results in near-complete disinfection within 120 seconds, within 60 seconds, with 30 seconds, within 20 seconds, within 10 seconds, or within 5 seconds.

In some embodiments, the surface is a surface of skin tissue, a surface of food or produce, a surface of an object or a device interface. In some embodiments, the device interface comprises a touchpad, a button, a knob, a dial, a switch, a touchscreen, a key, a keyboard, or the like.

In one example, the disclosed plasma applicator can be used to disinfect or sanitize various objects, such as a medical device. In another example, the disclosed plasma applicator can be used to disinfect or sanitize personal protective equipment (PPE), such as a face mask or respirator (e.g., surgical masks, activated carbon masks, N95, N-99, N-100, R-95, R-99, R100, P-95, P-99, or PI00 protective masks, etc.) to reduce the spread of pathogens (e.g., bacteria, viruses). Examples of bacteria may include, without limitation, *Pseudomonas aeruginosa, Staphylococcus aureus, Aspergillus brasiliensis* spores, *Brucella* species, *Burkholderia pseudomallei, Burkholderia mallei, Coxiella burnetii,* and *Escherichia coli.* Examples of viruses may include, without limitation, influenza viruses, rhinoviruses, adenoviruses and respiratory syncytial viruses, and the like. A further pathogen that may be protected against is the coronavirus, e.g., SARS-CoV, COVID 19.

Similarly, a plasma application of the present invention can be used to disinfect or sanitize wheels of a cart (e.g., shopping cart) to prevent the cart from spreading microorganisms or viruses.

In some embodiments, the predetermined distance is between about 0.1 cm and about 10 cm. In some embodiments, the step of applying comprises applying the AC input with a frequency of about 1 kHz to about 10 kHz to the plasma applicator. In some embodiments, the step of applying comprises applying the AC input with a frequency of about 1.0 kHz to about 3.5 kHz to the plasma applicator. In some embodiments, the AC input has a peak-to-peak voltage (Vp-p) ranging from about ±0.5 kV to about ±5 kV. In some embodiments, the AC input has a peak-to-peak voltage (Vp-p) ranging from about ±2.0 kV to about ±3.5 kV. In some embodiments, the step of applying comprises applying the AC input with a voltage of about 1 kV to about 100 kV to the plasma applicator. In some embodiments, the predetermined amount of time is between about 5 seconds and about 5 minutes.

iv. Self-Sanitizing Article

In one example, this disclosure provides a self-sanitizing article comprising the plasma applicator. In some embodiments, the article comprises a device controlling interface, such as a touchpad (e.g., a capacitive touchpad), a button, a knob, a dial, a switch, a touchscreen, a key, a keyboard or the like.

One particular use of the plasma applicators of the present invention is coupled with capacitive touch technology. A capacitive touch input, such as a touchpad, may be attached to a plasma applicator of the present invention. When contact is made with the capacitive touch input, the plasma applicator may be activated. The touch input may be placed directly on an exposed surface of a plasma applicator of the present invention, or a plasma applicator of the present invention may be incorporated into a surface comprising a capacitive touchpad. Accordingly, in such embodiments of the present invention, when the capacitive touchpad is touched, the plasma generator is activated, and the touchpad is self-sanitized. This would address a significant concern of touch-based interfaces and surfaces as a fomite, especially in a healthcare setting or other setting where contamination is a concern. Self-sanitizing touchpads are examined in Example 4 infra.

In another example, the plasma applicators of the present invention can be used to form self-sanitizing PPE, such as face mask or respirator, to protect against pathogens (e.g., airborne pathogens), such as the coronavirus, e.g., SARS-CoV, COVID 19.

The terms "pathogen" and "pathogenic agent" are interchangeable and, as used herein, mean any agent that can cause disease or a toxic substance produced by a pathogen that causes disease. Typically, the pathogenic agent will be a living organism that can cause disease. By way of example, a pathogen may be any microorganism, such as bacterium, protozoan or virus, that can cause disease. The term "airborne pathogen" means any pathogen which is capable of being transmitted through the air and includes pathogens that travel through air by way of a carrier material and pathogens either artificially aerosolized or naturally occurring in the air.

The face mask or respirator may include those that cover a health care personnel's, patient's, or a person's nose or mouth, and even preferably, a portion of the wearer's face, i.e., cheeks, jaw, chin, and so forth. In one embodiment, a respirator contemplated for use in the subject invention is an N95, N-99, N-100, R-95, R-99, R100, P-95, P-99, or PI00 respirator. In a specific embodiment, the respirator is an N-95 respirator.

In some embodiments, the article comprises a wheel. For example, the article can be a wheel for a cart (e.g., a shopping cart), such that the wheel can be self-sanitized, thus preventing the cart from spreading bacteria or viruses.

v. Handheld Device

Another particular use of the plasma applicators of the present invention is in a device that contains inserts, optionally replaceable or disposable, comprising the plasma applicators as disclosed herein, a housed electricity source, e.g., a battery, optionally rechargeable, and a handle or other means for a user to hold. Optionally, the electricity source could be stored in the handle. A user would be able to activate the plasma applicator via, e.g., a button, switch, or other on/off means. Alternatively, the handheld device may utilize the touchpad technology disclosed herein, including the self-sanitizing touchpad. Such handheld devices would be especially attractive for home use or private consumers and are achievable due to the low cost of the materials involved in constructing the plasma applicators of the present invention.

vii. Disposable Garments

Yet another particular use of the plasma applicators of the present invention would be in disposable garments, e.g., paper-based disposable garments. Protective garments are examined in Example 5 infra.

viii. Kirigami-Based Applications

Kirigami is a variation of origami that includes cutting of paper rather than folding the paper. Kirigami typically starts with a folded base, which is subsequently unfolded. Cuts are then opened and flattened to create the finished kirigami product. Kirigami products are typically symmetrical and employ a degree of flexibility that may be advantageous for incorporation in the plasma applicators of the present invention. Kirigami-like plasma generators may be especially useful for creating conformable electronics that require stretching or bending about more than one axis. Kirigami-based applications are examined in Example 6 infra.

ix. Package Based Applications

The plasma applicators of the present invention may be included in packaging, such as packaging for foodstuffs. In such embodiments, the plasma applicators would be included on an interior surface of the packaging, so that the plasma applicators are facing the materials, e.g., foodstuffs or other articles to be sanitized. The exterior of the packaging could optionally contain contact points that connect to a metal surface of the plasma applicators contained within the packaging; such contacts would be capable of coming in contact with a high voltage source so as to activate the plasma applicators without actually having to open the packaging up, allowing for rapid disinfection of the materials within the packaging without disturbing the integrity of the overall packaging. The plasma applicators contained with the packaging may also contain a non-conductive spacer, similar to the bandages, that may protect the contents of the package from coming in direct contact with the plasma applicators.

x. Devices for Deodorization

In another example, this disclosure further provides a system for deodorizing an object that comprises the plasma applicator described above. In some embodiments, the object comprises an article of footwear or a fabric product.

Accordingly, this disclosure also provides a method of deodorizing an article using a plasma applicator. The method comprises (a) placing a plasma applicator over a surface of the article and thereby to cause the plasma applicator to directly contact the surface or to maintain a predetermined distance over the surface; and (b) applying an AC input from the high voltage source and keeping the plasma applicator over the surface for a predetermined amount of time, thereby causing the plasma applicator to generate DBD-based plasma that reduces odor from the article.

In some embodiments, the article comprises an article of footwear or various fiber products, such as yarns, woven fabrics, knitted fabrics, nonwoven fabrics, pile fabrics, pile fabrics such as pile fabrics, and the like. Examples include formed clothing and other body wear items, interior products, bedding, and food packaging materials. Specifically, clothing and body such as underwear, sweater, jacket, pajamas, yukata, white robe, slacks, socks, gloves, stockings, apron, mask, towel, handkerchief, supporter, head hand, hat, shoe insole, interlining wearing items, various carpets, curtains, goodwill, wallpaper, shoji paper, cocoons, textile blinds, artificial ornamental plants, fabrics for upholstery such as chairs, table cloths, electrical product covers, tatami mats, futon filling, etc.), duvet side, sheets, blankets, duvet covers, pillows, pillow covers, bed covers, bed filling materials, mats, sanitary materials, toilet seat covers, wiping cloths, or filters.

xi. Devices for Oxidation

In another example, this disclosure also provides a device comprising the plasma applicator for oxidizing an article. In some embodiments, the article is a gas sensor and wherein the DBD-based plasma is configured to oxidize the sensor and thereby to reset the gas sensor. Oxidation is a process useful for fabricating many types of sensors, including gas sensors. Gas sensors and biosensors work by collecting organic or other oxidizable materials. The electrodes of many gas sensors do not require functionalization with organics to capture and sense gases (e.g., methane and ammonia). When these sensors capture these gases, they can saturate, which requires time to clear the collected chemicals. In this context, the cold plasma produced by the disclosed plasma applicator can be used to strip these captured chemicals and "reset" sensors for accurate new measurements.

Accordingly, this disclosure further provides a method of oxidizing an object. The method comprises (i) placing the plasma applicator over a surface of the article and thereby to cause the plasma applicator to directly contact the surface or to maintain a predetermined distance over the surface; and (2) applying an AC input from the high voltage source and keeping the plasma applicator over the surface for a predetermined amount of time, thereby causing the plasma applicator to generate DBD-based plasma that oxidizes the article. In some embodiments, the article is a gas sensor and wherein the DBD-based plasma is configured to oxidize the sensor and thereby to reset the gas sensor.

C. Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope to of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

D. Examples

1. Ozone Generation

In order to demonstrate the plasma generation of the plasma applicators, the corresponding ozone level ($O_3$) generated by the plasma applicators of the present invention was measured in parts-per-million (ppm) over time and displayed in TABLE 1 below. The plasma applicators were constructed according to the structure set forth in exemplary FIG. 1 and FIG. 2, with each substrate layer constructed with a base layer comprising paper, two successive polymeric layers on top of the base layer, vacuum evaporated aluminum comprising the metallic surface layer on top of the second polymeric layer, and a layer of polymeric coating covering the metallic surface layer. The plasma applicator was constructed according to FIG. 1, with an adhesive layer binding the base layers of both substrate layers to each other such that the conductive polymeric-coated metallic surface layers were exposed. Conductive silver ink was placed on the contact points for the plasma applicator. The level of UV-C radiation detected was 1.9 mW/cm$^2$/nm, the surface temperature was reported as 60° C. within 60 seconds of activation, and a high level of ozone (approximately 13 ppm within 60 seconds of activation) was observed.

TABLE 1

Ozone concentration generated by plasma applicator.

| Time (s) | Ozone Concentration (ppm) |
|---|---|
| 5 | 5.56 |
| 10 | 7.23 |
| 20 | 9.81 |
| 30 | 8.97 |
| 60 | 13.53 |
| 120 | 27.34 |

2. Non-Contact (Indirect Contact) Experiments

Non-contact experiments were carried out with the plasma applicators of the present invention. In these experiments, the plasma applicators were designed according to the criteria set forth as described in section IV(B)(ii) above, with both substrate layers designed with laser-etched "honeycomb" shaped metallic surface layers. The plasma applicators were constructed according to the structure set forth in exemplary FIG. 1 and FIG. 2, with each substrate layer constructed with a base layer comprising paper, two successive polymeric layers on top of the base layer, vacuum evaporated aluminum comprising the metallic surface layer on top of the second polymeric layer, and a layer of polymeric coating covering the metallic surface layer. The plasma applicator was constructed according to FIG. 1, with an adhesive layer binding the base layers of both substrate layers to each other such that the conductive polymeric-coated metallic surface layers were exposed. Conductive silver ink was placed on the contact points for the plasma applicator. Each plasma applicator had a diameter of 90 mm, matching the inner diameter of the lid of a Petri dish. By attaching the plasma applicator to the inner surface of the Petri dish lid, the plasma applicator was not directly contacted, which avoided unintentional contamination. When closed, the surface of the plasma applicator was 10 mm away from the surface of the media. For both experiments 1 and 2, the voltage applied to the plasma applicator was 6.3 kV, and the frequency was set to 2 kHz.

For both Examples 2 (indirect contact) and 3 (direct contact), S. cerevisiae strain AH109 (Clontech Laboratories, Inc.) and E coli strain TOP 10 (Invitrogen) served as samples of fungus and bacteria. AH109 is a yeast strain usually used for two-hybrid screening, and TOP10 is an ideal bacterial strain for high-efficiency cloning and plasmid propagation. AH109 and TOP10 were cultured with yeast extract peptone dextrose (YEPD) medium and lysogeny broth (LB), respectively. The YEPD broth contained 1% (m/v) yeast extract (Difco), 2% (m/v) peptone (Sigma-Aldrich Corp.), 2% (m/v) dextrose (VWR international), with the remainder being distilled water. The YEPD solid medium contained 0.3% (m/v) yeast extract, 1% (m/v) peptone, 1% (m/v) dextrose, 2% (m/v) agar (Difco), with the remainder being distilled water. LB was prepared with the dehydrated culture medium of Luria-Bertani (Difco) and proper hydration with distilled water. The preferred LB medium contained 2.5% (m/v) LB powder, the rest being distilled water. The LB solid medium contained 2.5% (m/v) LB powder, 1.5% (m/v) agar, the rest being distilled water. Autoclavation of all media lasted for 20 minutes at 121° C. For both the solid media of YEPD and LB, 25 mL of media was contained in each Petri dish. AH109 and TOP10 were cultured in 150 RPM in an orbital incubator shaker (Model 3527, Lab-Line Instrumentations Inc.) for 24 hours at room temperature. The microbes were collected by centrifuging (Clinical 100, VWR International) the cultures at 4000 RMP for 5 minutes. Both AH109 and TOP10 cells were in suspension with sanitized distilled water. To determine the concentration of AH109 and TOP10 in the suspension, a spectrophotometer (Genesys 10s UV-VIS, Thermo Scientific) was utilized to measure the $OD_{600}$. The measured $OD_{600}$ of AH109 and TOP10 were 1.037 and 0.867 respectively, indicating concentrations of approximately $6.22 \times 10^7$ cells/mL and $6.94 \times 10^8$ cells/mL respectively. The concentrations were diluted to $2.07 \times 10^3$ cells/mL and $2.50 \times 10^4$ cells/mL respectively.

A. Experiment 1—S. cerevisiae

Figure 5A:
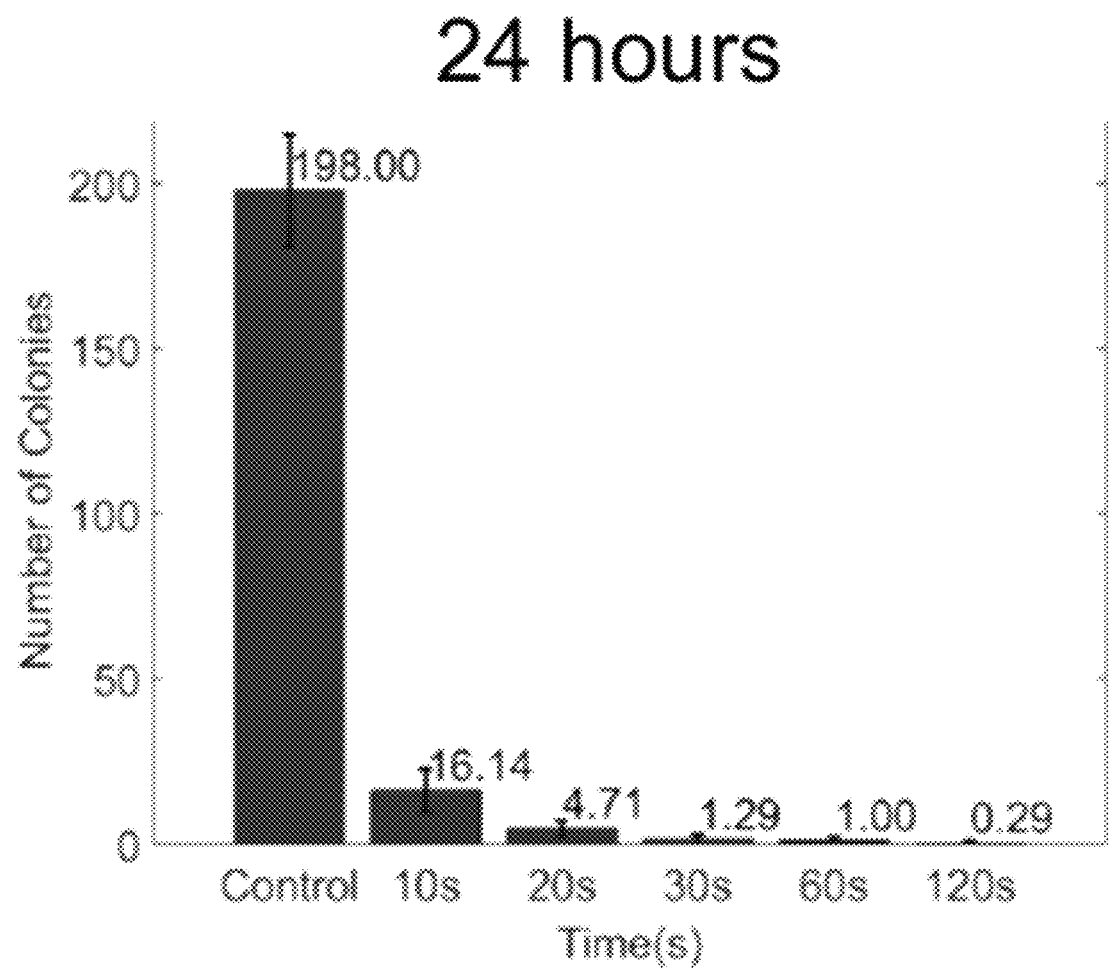
FIG. 5A represents average colony counts at 24 hours for the six Saccharomyces cerevisiae (S. cerevisiae) indirect contact experimental groups.
Figure 5B:
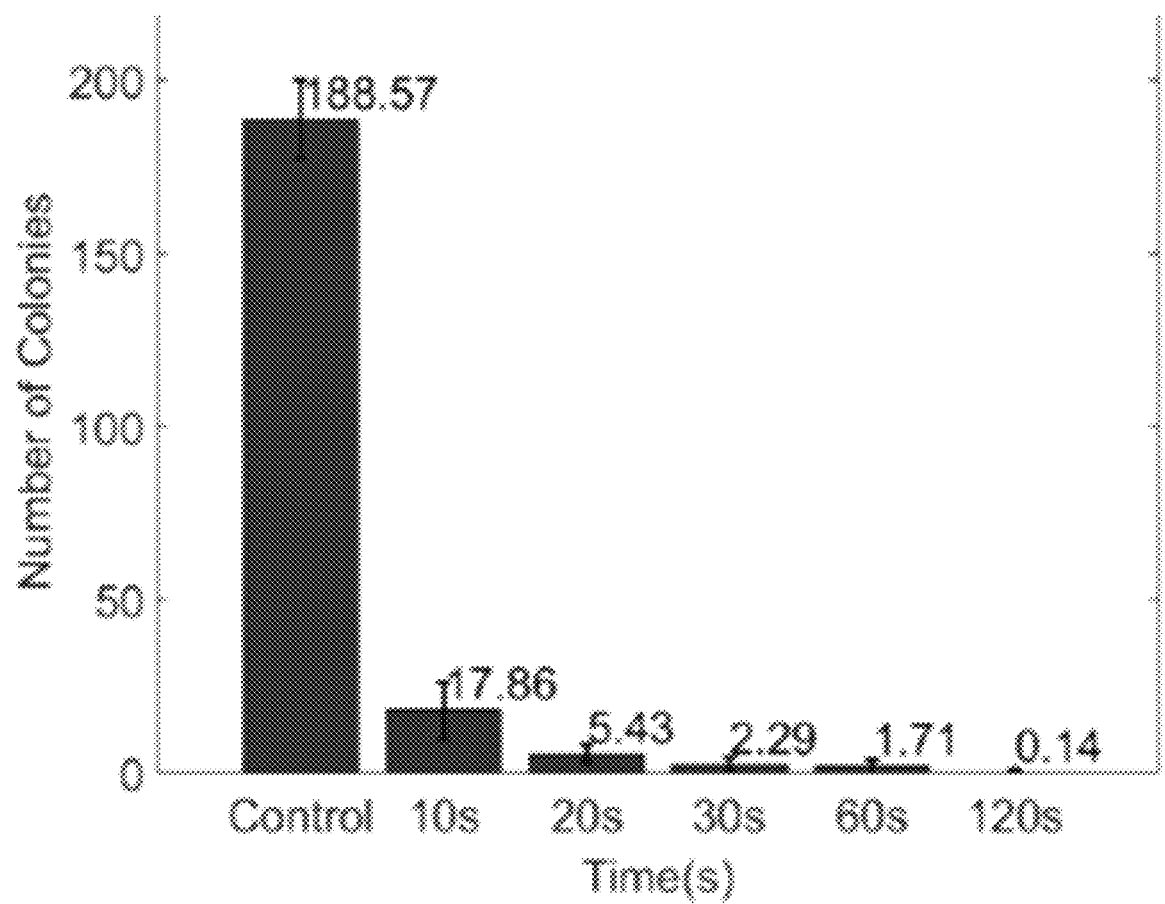
FIG. 5B represents average colony counts at 48 hours for the six S. cerevisiae indirect contact experimental groups.

The plasma applicator was pre-sanitized by standard UV sanitation procedures. The plasma applicator, as described, was placed in a covered petri dish at a distance of 10 mm from the surface of a medium consisting of yeast extract peptone dextrose (YEPD). The test target for Experiment 1 was S. cerevisiae at a concentration of $3.6 \times 10^4$ unit/mL. This was achieved by inoculating 100 μL of S. cerevisiae cell suspensions on the YEPD media. The lead of the circular applicator ran through the gap between the lid and the Petri dish to an AC input with a frequency of 2 kHz and a peak-peak voltage of ±3.15 Kv. There was a total of 6 testing groups (5+1 control), with each testing group corresponding to a different length of time for which plasma was generated (i.e., the plasma applicator was active): 10 seconds, 20 seconds, 30 seconds, 60 seconds, and 120 seconds. The number of resultant colonies was recorded for each testing group at 24 hours and 48 hours. The experiment was repeated seven times for each group, and the results were averaged and displayed in FIG. 5A (24 hours) and FIG. 5B (48 hours).

B. Experiment 2—E. coli

Figure 6:
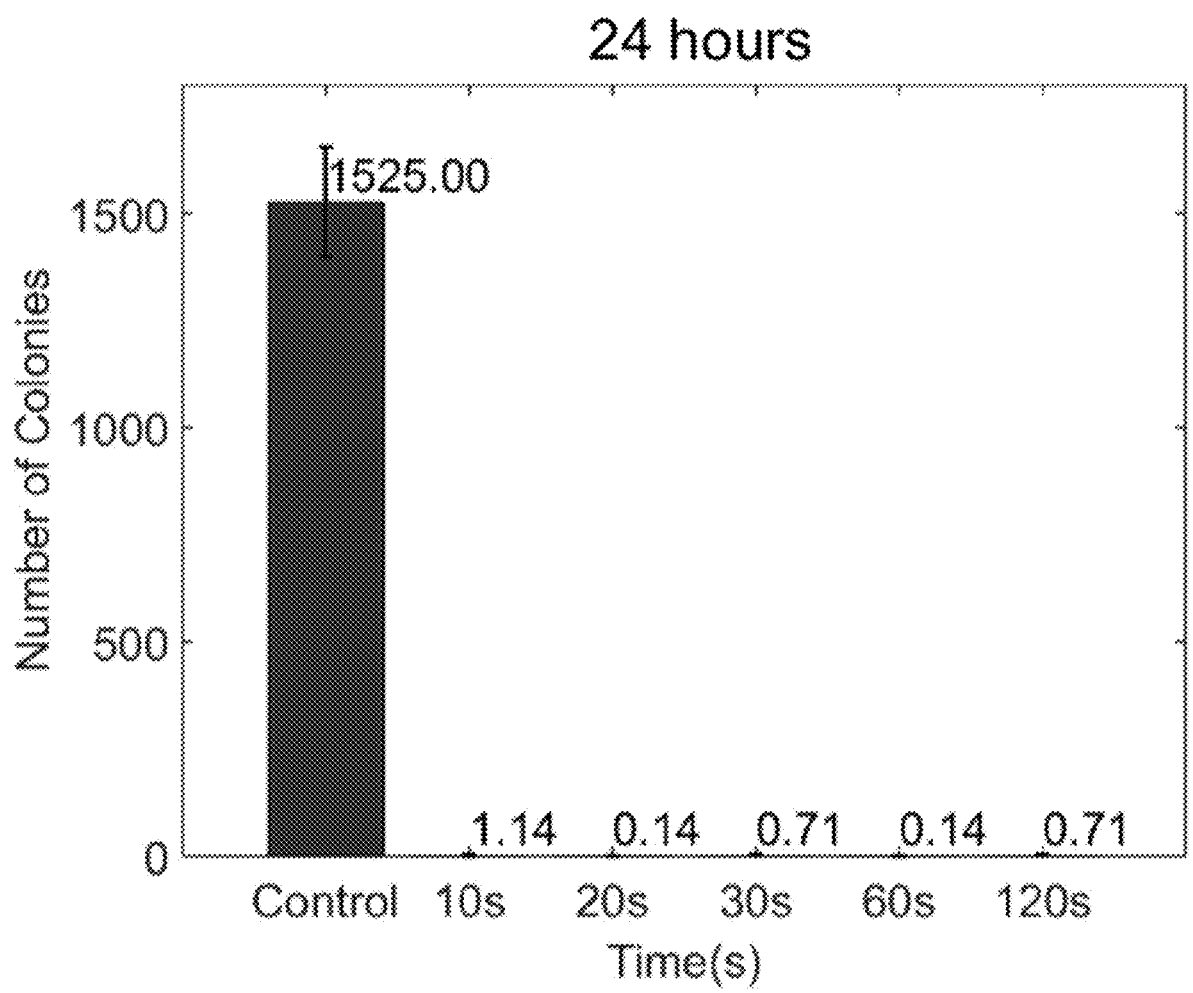
FIG. 6 represents average colony counts at 24 hours for the six Escherichia coli (E. coli) indirect contact experimental groups.

The plasma applicator was pre-sanitized by standard UV sanitation procedures. The plasma applicator, as described, was placed in a covered petri dish at a distance of 10 mm from the surface of a medium consisting of lysogeny broth (LB). The test target for Experiment 2 was E. coli at a concentration of $3.6 \times 10^4$ unit/mL. This was achieved by inoculating 100 μL of E. coli cell suspensions on the LB media. The lead of the circular applicator ran through the gap between the lid and the Petri dish to an AC input with a frequency of 2 kHz and a peak-peak voltage of ±3.15 kV. There was a total of 6 testing groups (5+1 control), with each testing group corresponding to a different length of time for which plasma was generated (i.e., the plasma applicator was active): 10 seconds, 20 seconds, 30 seconds, 60 seconds, and 120 seconds. The number of resultant colonies was recorded for each testing group at 24 hours. The experiment was repeated seven times for each group, and the results were averaged and displayed in FIG. 6.

C. Results

After 10 seconds of active treatment, the mean number of colonies decreased to 16.14, signifying an inactivation rate of 91.85%. After 20 seconds and 30 seconds of treatment, the inactivation rate for S. cerevisiae became 97.89% and 99.34%, respectively. With respect to E. coli, within 10 seconds of treatment, the resulting inactivation rate was as high as 99.93%. Treatments longer than 10 seconds resulted in an average of less than 1 remaining colony, representing efficiencies greater than 99%. The results thus indicate efficiencies as high as 99% with treatment times of only 30 seconds.

The decimal reduction time, or D-value, is the time required at a given condition (e.g., temperature) or set of conditions to kill 90% (1 log) of exposed microorganisms in a sample. Calculation of D-value is set forth in the equation below:

$$D\text{-value}=t/[\log(N_0)-\log(N_t)]$$

wherein $N_0$ is the initial population and $N_t$ is the population at the end of the test.

Based on the results of experiments 1 and 2 of Example 2 (indirect contact), the calculated D-values for both S cerevisiae and E. coli were less than 10 seconds, illustrating the surprising efficacy of the plasma applicators in an indirect contact scenario.

3. Direct Contact Experiments

Direct contact experiments were carried out with the plasma applicators of the present invention. In these experiments, the plasma applicators were designed according to the criteria set forth as described in section IV(B)(ii) above, with both substrate layers designed with laser-etched "honeycomb" shaped metallic surface layers. The plasma applicators were constructed according to the structure set forth in exemplary FIG. 1 and FIG. 2, with each substrate layer constructed with a base layer comprising paper, two successive polymeric layers on top of the base layer, vacuum evaporated aluminum comprising the metallic surface layer on top of the second polymeric layer, and a layer of conductive polymeric coating covering the metallic surface layer. The plasma applicator was constructed according to FIG. 1, with an adhesive layer binding the base layers of both substrate layers to each other such that the conductive polymeric-coated metallic surface layers were exposed. Conductive silver ink was placed on the contact points for the plasma applicator.

These experiments were carried out in an experimental setup to simulate a human sneeze and test the efficacy of the plasma applicators of the present invention. Experiments 1 and 2 pre-sanitized the plasma applicator with UV sanitation techniques prior to simulation of a human sneeze, while experiments 3 and 4 did not pre-sanitize the plasma applicator. Hence, experiments 3 and 4 illustrate not only the ability of the plasma applicators to sanitize the microbes in the simulated human sneeze, but also unknown microbes on the surface of the non-sanitized plasma applicators.

For experiments 1, 2, 3, and 4, a human sneeze was simulated through use of the Nordson EFD Precision dispensing system (Performus II, Nordson EFD), a droplet dispensing machine which can precisely control the amount of liquid it dispenses each time. Each simulated sneeze contained either diluted *S. cerevisiae* at a concentration of $3.5 \times 10^8$ unit/mL (experiments 1 and 3) or *E. coli* at a concentration of $3.6 \times 10^8$ unit/mL (2 and 4). Using a gauge pressure of 11 psi and a dispensing time of 50 μs, an intranasal drug delivery device (MAD Nasal, LMA) atomized a liquid suspension of *S. cerevisiae* (experiments 1 and 3) or *E. coli* (experiments 2 and 4) onto the plasma applicators. The simulated sneeze was dropped directly onto the surface of the plasma applicator, which for all 4 experiments was repeated for plasma generation times of 0 seconds (Control), 5, 10, 20, 30, and 60 seconds. A blank control (BC) was also used, which contained the same type of paper-based plasma applicator but was not activated. After plasma generation, the plasma applicator came in direct contact with a petri dish, which was then incubated at 30° C. for 48 hours to observe growth.

A. Experiment 1—*S. cerevisiae*

Figure 7:
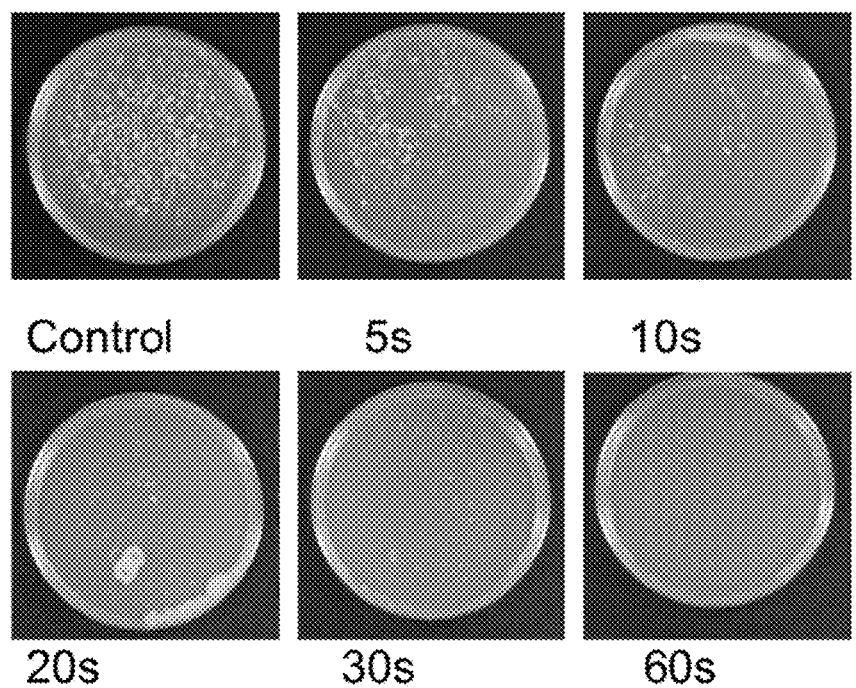
FIG. 7 represents the results of the direct contact experiments for S. cerevisiae experimental groups.

The plasma applicator was pre-sanitized by standard UV sanitation procedures. After coming in contact with a simulated sneeze and generating plasma for a set length of time, the plasma applicator, as described above, was placed in a covered petri dish directly contacting the surface of a medium consisting of yeast extract peptone dextrose (YEPD). The test target for Experiment 1 was *S. cerevisiae* at a concentration of $3.5 \times 10^8$ unit/mL. There was a total of 6 testing groups (5+1 control), with each testing group corresponding to a different length of time for which plasma was generated (i.e., the plasma applicator was active): 5 seconds, 10 seconds, 20 seconds, 30 seconds, and 60 seconds. The results are shown in FIG. 7.

B. Experiment 2—*E. coli*

Figure 8:
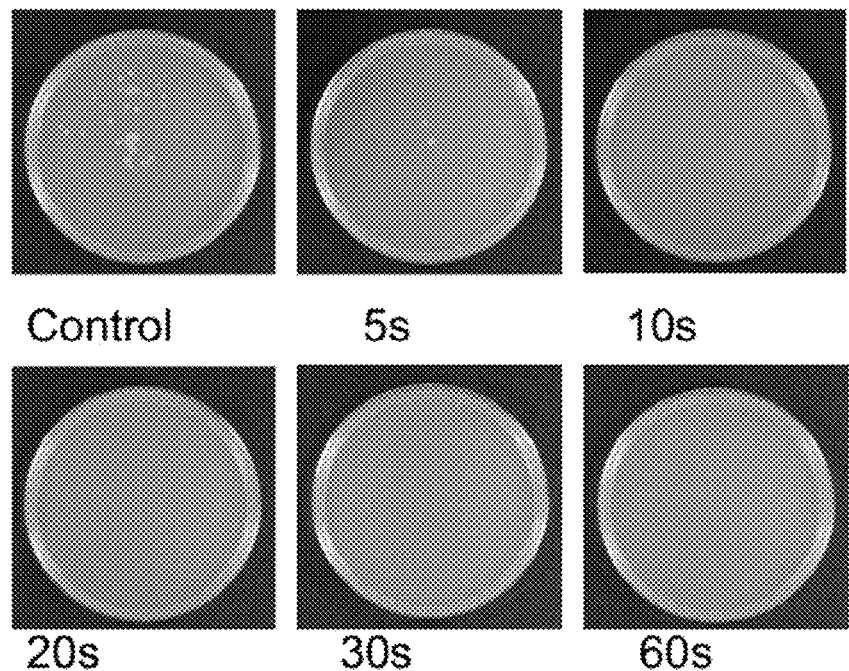
FIG. 8 represents the results of the direct contact experiments for E. coli experimental groups.

The plasma applicator was pre-sanitized by standard UV sanitation procedures. After coming in contact with a simulated sneeze and generating plasma for a set length of time, the plasma applicator, as described, was placed in a covered petri dish directly contacting the surface of a medium consisting of lysogeny broth (LB). The test target for Experiment 2 was *E. coli* at a concentration of $3.6 \times 10^8$ unit/mL. There was a total of 6 testing groups (5+1 control), with each testing group corresponding to a different length of time for which plasma was generated (i.e., the plasma applicator was active): 5 seconds, 10 seconds, 20 seconds, 30 seconds, and 60 seconds. The results are shown in FIG. 8.

C. Experiment 3—*S. cerevisiae* with Contamination

Figure 9:
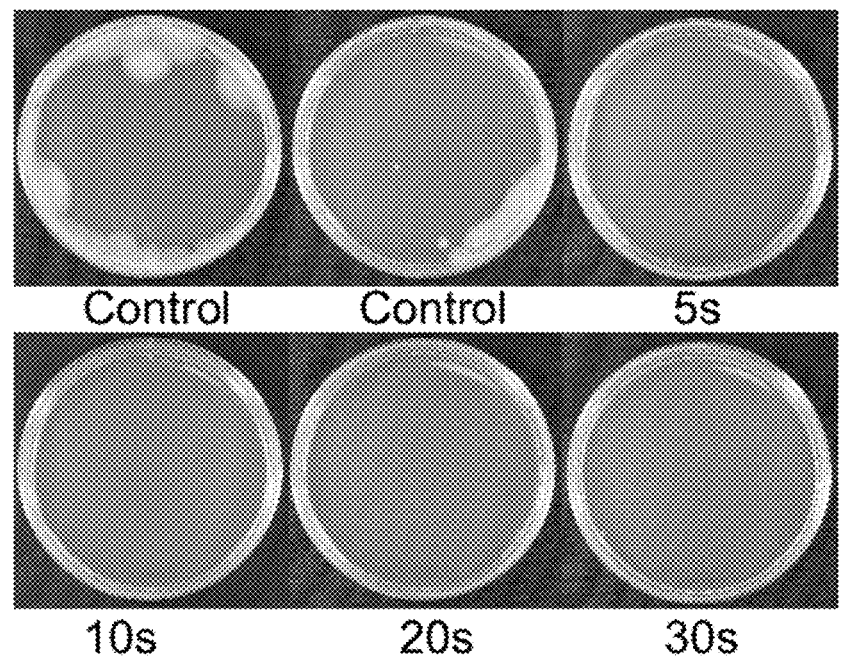
FIG. 9 represents the results of the direct contact experiments for S. cerevisiae experimental groups, where the plasma applicator was not disinfected prior to the direct contact.

The plasma applicator was not pre-sanitized by standard UV sanitation procedures (i.e. "with contamination.") After coming in contact with a simulated sneeze and generating plasma for a set length of time, the plasma applicator as described was placed in a covered petri dish directly contacting the surface of a medium consisting of yeast extract peptone dextrose (YEPD). The test target for Experiment 3 was contaminated *S. cerevisiae*. There was a total of 6 testing groups (5+1 control), with each testing group corresponding to a different length of time for which plasma was generated (i.e., the plasma applicator was active): 5 seconds, 10 seconds, 20 seconds, 30 seconds, and 60 seconds. The results are shown in FIG. 9. The contamination was later revealed to be *Bacillus*.

D. Experiment 4—*E. coli* with Contamination

Figure 10:
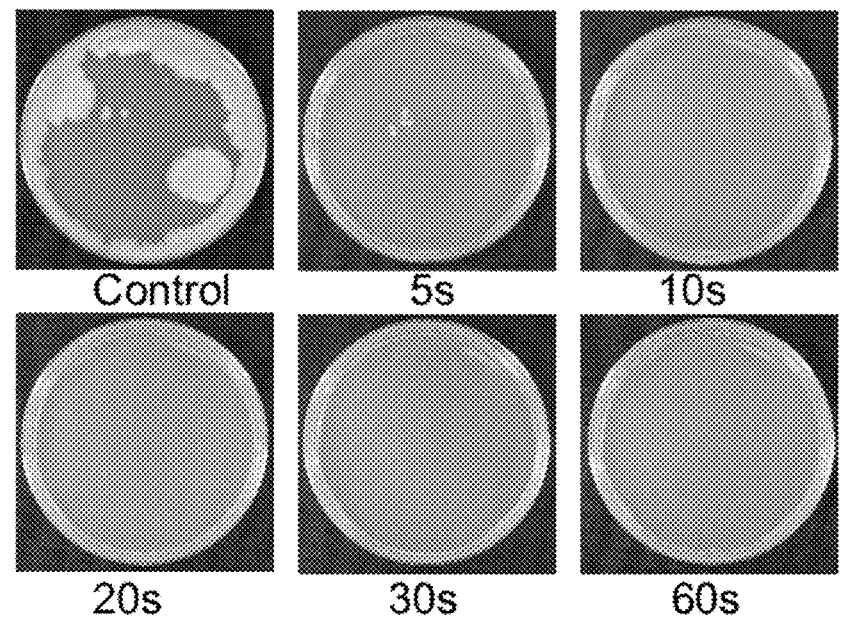
FIG. 10 represents the results of the direct contact experiments for S. cerevisiae to experimental groups, where the plasma applicator was not disinfected prior to the direct contact.

The plasma applicator was not pre-sanitized by standard UV sanitation procedures (i.e. "with contamination.") After coming in contact with a simulated sneeze and generating plasma for a set length of time, the plasma applicator as described was placed in a covered petri dish directly contacting the surface of a medium consisting of lysogeny broth (LB). The test target for Experiment 4 was contaminated *E. coli*. There was a total of 6 testing groups (5+1 control), with each testing group corresponding to a different length of time for which plasma was generated (i.e., the plasma applicator was active): 5 seconds, 10 seconds, 20 seconds, 30 seconds, and 60 seconds. The results are shown in FIG. 10. The contamination was later revealed to be *Bacillus*.

E. Results

Figure 11:
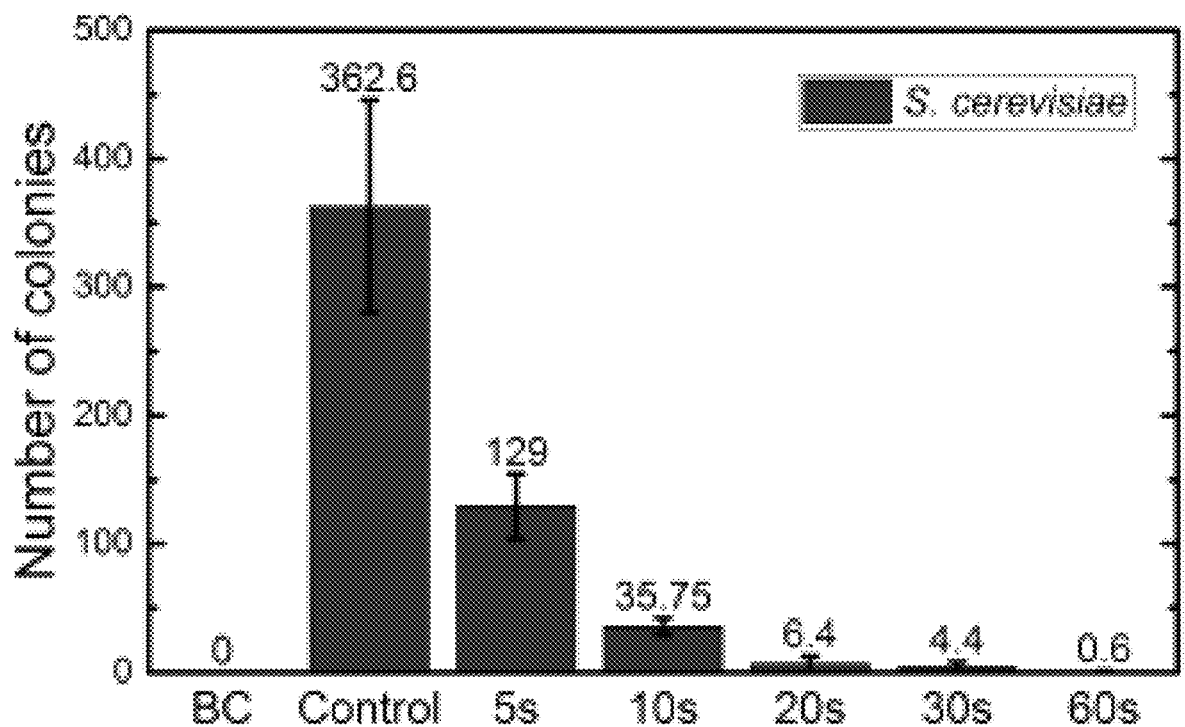
FIG. 11 represents a histogram showing the number of colonies formed by S. cerevisiae after being incubated for 48 hours in the direct contact experiments.
Figure 12:
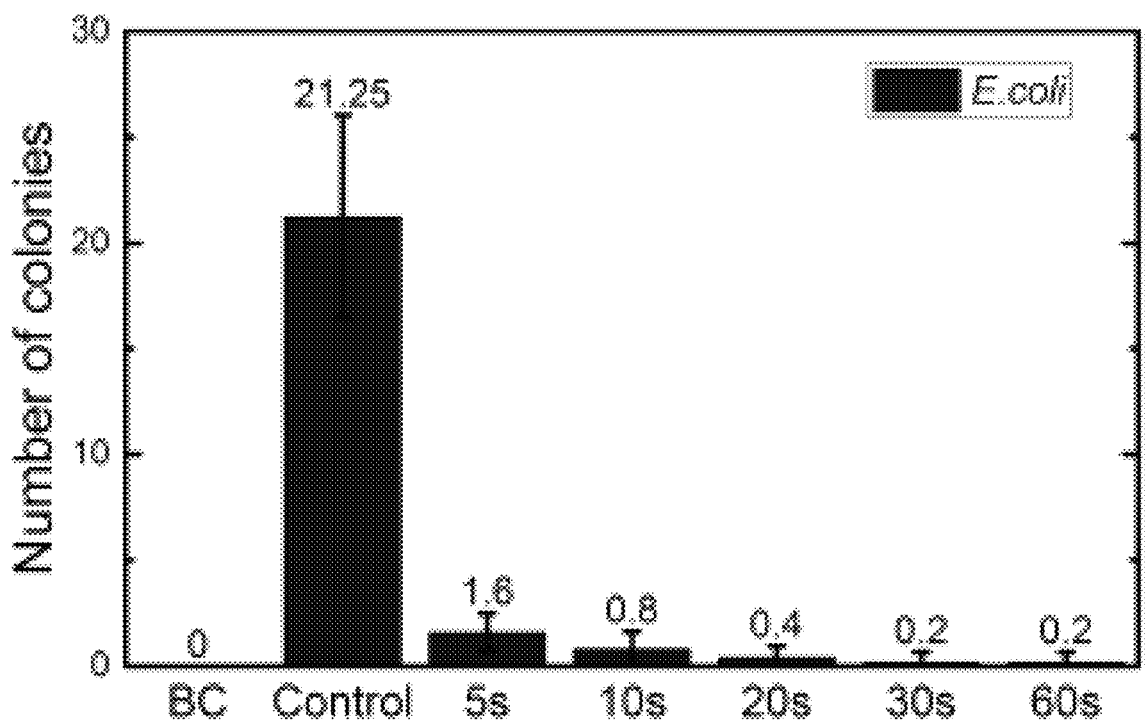
FIG. 12 represents a histogram showing the number of colonies formed by E. coli after being incubated for 48 hours in the direct contact experiments.

Quantitative results (histograms) for *S cerevisiae* and *E. coli* are shown in FIG. 11 and FIG. 12. The results indicated that with 60 seconds of plasma treatment, there were no observable cells on the YEPD media. With only 10 seconds of plasma treatment, there were no observable colonies on the LB media.

The substrate layers (metalized paper) of the plasma applicators are not inherently sterile products, thus likely containing contaminants on the surface and within the porous structure. This was the basis behind the "with contamination" testing protocols, as during testing, non-specific contaminants/colonies were observed in those scenarios where the plasma applicator was not pre-sanitized. Notably, however, none of the samples appeared to be contaminated after 30 seconds of active plasma generation. Thus, the results indicate that by generating volume plasma, in particular, the plasma applicators self-sanitized by removing the contaminant (bacillus) from the fibrous interior of the substrate layers.

4. Self-Sanitizing Touchpads

The plasma applicators of the present invention can be incorporated into self-sanitizing touchpads, e.g., capacitive touchpads. Capacitive touchpads using, for example, metalized paper (an exemplary substrate layer of the present invention), are disclosed in Mazzeo A D, et al. (2012) Paper-Based, Capacitive TouchPads., *Adv. Mater* 24(21): 2850-2856, hereby incorporated by reference in its entirety. By integrating plasma applicators of the present invention with capacitive touchpads, these devices are capable of sanitizing themselves after being touched. The operation occurred as follows. A button was touched with two fingers to activate corresponding LEDs as well as activating the plasma to sanitize the buttons with a frequency of 500 Hz and a $V_{p-p}$ of ±2.5 kV. The conductive traces on the touchpad were at least 2.5 mm away from each other, as narrower gaps resulted in discharges and non-uniform ablation of the conductive layer (evaporated aluminum).

5. Paper-Based Disposable Garments

To demonstrate the use of the plasma applicators in garment-like systems, a rectangular, paper-based band with half the surface area covered with a hexagonal, conductive layer was prepared. There was no conductive layer on the other half of the band as it was removed via laser ablation. The design thus produced plasma only on the half of the band that contained a conductive layer. The other half was reserved as a control group with Kapton tape attached to the surface.

The paper-based band was wrapped around an individual's wrist and was then sprayed with an atomized suspension of *E. coli* on the surface of the band to ensure approximately equal distribution of the *E. coli*. The concentration of the suspension was calculated as approximately $3 \times 10^8$ cells/mL. The band was then removed from the individual's wrist and connected to electrodes. The plasma applicator was activated under the excitation of an AC source with a peak-to-peak voltage of ±2.3 kV and a frequency of 1.7 kHz. After activating the plasma applicator, the electrodes were removed, and the cells were transferred to the surface of a pre-prepared lysogeny broth (LB) medium. The medium was incubated at 37° C. for 48 hours. From a qualitative perspective, the number of resultant colonies was inversely proportional to the duration of plasma treatment.

6. Kirigami-Like Plasma Generators

A kirigami-based device comprising the plasma applicators of the present invention (utilizing metalized paper as the substrates) was constructed with an initial geometry of a 2-D square. When stretched, it opened into a 3-D structure. An external voltage source was applied to the kirigami device, which resulted in an excitation frequency of 500 Hz while the peak-to-peak voltage was ±2.5 kV.

7. Plasma Applicators for Sanitizing Food and Produce

In this example, the application of the plasma applicators of the present invention for use in sanitizing food or produce (e.g., tomatoes, baby spinach) is described. Sinusoidal signals were produced with frequencies ranging from 100 Hz to 2 kHz and peak-to-peak voltages (Vp-p) of ±9.5 V using a function generator (4011A; BK Precision). Then, the signal was amplified using a high voltage amplifier (model 10/10; TREK) that has a gain of 1 kHz to output a high oscillating potential Vp-p of ±9.5 kV. The generation of plasma depends on the frequency of the alternating current, suggesting that uniform plasma generates at an optimal frequency at a particular voltage. The power consumption of both paper-based plasma generators demonstrated in this work was 43.7 W for RMS 6.8 kV at ~6.43 mA and 73.48 W for RMS 6.43 kV at ~11.43 mA going into the flat and two-cone conformable device respectively. Plasma activation times were for 2, 5, and 10 minutes. These devices were foldable into cones or flat with a diameter of 8 cm.

A. Evaluation of Microbial Inactivation Efficacy of Surface Dielectric Barrier Discharge (SDBD) Plasma (a) Inactivation on the Surface of Tryptic Soy Agar (TSA)

Figure 13C:
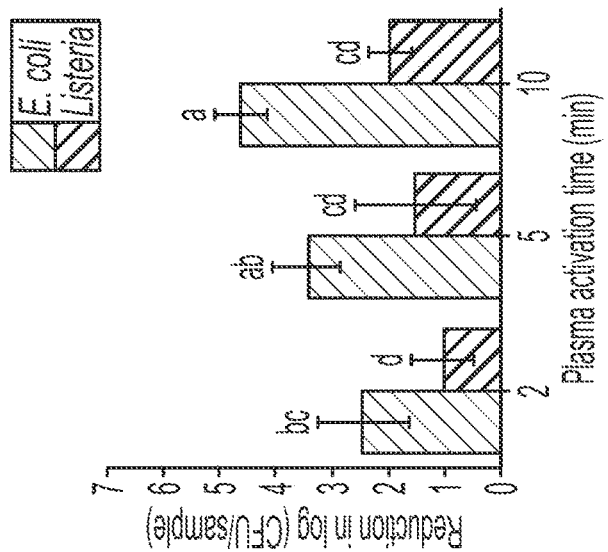
FIGS. 13A, 13B, and 13C are a set of graphs showing inactivation efficacy of surface dielectric barrier discharge (SDBD) plasma of various treatment time against E. coli and L. innocua inoculated on the surface of TSA (FIG. 13A), baby spinach leaves (FIG. 13B), and whole tomatoes (FIG. 13C). Mean±SD. Means sharing the same letter are non-significant at $P<0.05$ according to Tukey's HSD test.

Before applying the SDBD plasma to the food products, the plasma treatment against *E. coli* and *L. innocua* on the surface of TSA was evaluated (FIG. 13A) to show the inactivation efficacy of this technique on a flat and smooth surface, without the interfering of the complicated characteristics of food surface. The initial load of cells inoculated on the TSA plate was 6.8±0.1 log CFU/sample for *E. coli* and 7.2±0.5 log CFU/sample for *L. innocua*. After treatment for 2 minutes, 5 minutes, and 10 minutes, the populations of *E. coli* were reduced by 3.0±0.2 CFU/sample, 4.3±0.2 CFU/sample, and 5.0±0.1 CFU/sample, while the reductions of *L. innocua* were 3.1±0.3 CFU/sample, 4.4±0.5 CFU/sample, and 4.8±0.4 CFU/sample. The reductions of both *E. coli* and *L. innocua* were significantly higher (p<0.05) after treatment for 5 minutes from that of 2 minutes. Interestingly, given the same plasma treatment time, there was no significant difference (p>0.05) between the numbers of reduction of the two bacteria. These results indicated that the circular SDBD electrodes could inactivate both bacteria with similar ~5-log inactivation efficacy for the 10-minute treatment on a smooth and flat surface like the surface of the TSA agar. The temperature of the air rose by 4° C. above the room temperature for the 10-minute plasma exposure—insignificant to deactivate bacteria. Therefore, the RONS and UV radiation were the main factors to deactivate bacteria.

(b) Inactivation on the Surface of Baby Spinach Leaf

Figure 13B:
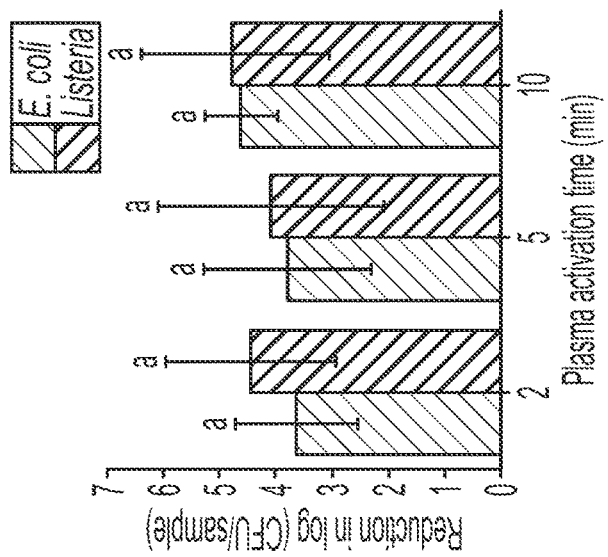
Figure 13A:
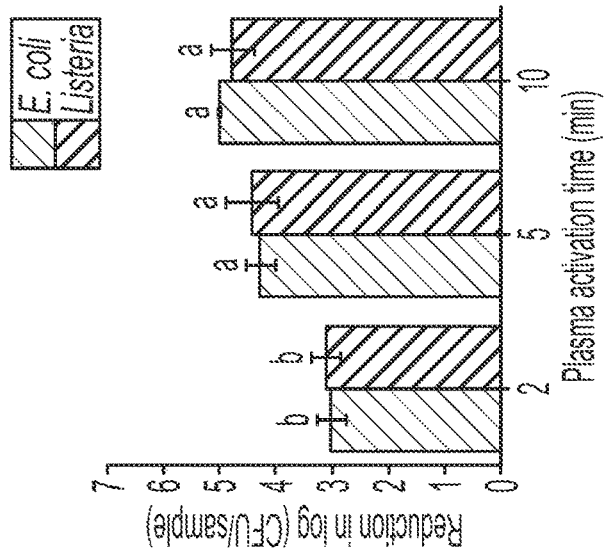

The inactivation of *E. coli* and *L. innocua* inoculated on the leaves of baby spinach was represented in FIG. 13B. The leaves were inoculated with an average of 5.7±0.9 log CFU/sample for *E. coli* and 7.6±0.5 log CFU/sample for *L. innocua*, respectively. After 2 minutes, 5 minutes, and 10 minutes of plasma treatment, populations of *E. coli* were reduced by 3.6±1.1 log CFU/sample, 3.7±1.5 log CFU/sample, and 4.6±0.6 log CFU/sample. No significant difference (p>0.05) in the number of reductions was observed among the three treatment times against *E. coli*. Similarly, populations of *L. innocua* were reduced by 4.4±1.5 log CFU/sample, 4.1±1.9 log CFU/sample, and 4.8±1.7 log CFU/sample after plasma exposure for 2 minutes, 5 minutes and 10 minutes, respectively, with no significant difference (p>0.05) detected from each other. In addition, at each treatment time, the reductions of *E. coli* and *L. innocua* were not significantly different (p>0.05).

Unlike the decontamination on the surface of TSA, the decontamination on spinach to leaves showed a larger variation, even though in both experiments, the same type of electrodes were used. This might be due to differences in surface topography between spinach leave and TSA plate. The roughness of spinach leaves varies among leaves, resulting in a large leaf-to-leaf variation regarding the inactivation efficacy of SDBD plasma towards both *E. coli* and *L. innocua*.

(c) Inactivation on the Surface of Whole Tomato

The inactivation of *E. coli* and *L. innocua* attached on the surface of whole tomatoes was shown in FIG. 13C. The initial load of cells attached on the tomato samples was 6.0±0.3 Log CFU/sample for *E. coli* and 7.5±0.4 log CFU/ sample for *L. innocua*. SDBD plasma treatment of 2 minutes, 5 minutes, or 10 minutes resulted in the reduction of 2.5±0.8 log CFU/sample, 3.4±0.6 log CFU/sample, and 4.6±0.5 CFU/sample. The inactivation efficacy increased as the increase of plasma treatment time, and the populations reduced treatment for 10 minutes was significantly higher ($p<0.05$) than that of 2 minutes. The reduction in populations of *L. innocua* also increased over the treatment time and was 1.0±0.5 log CFU/sample, 1.5±1.0 log CFU/sample, and 2.0±0.4 log CFU/sample after treatment for 2 minutes, 5 minutes, and 10 minutes, respectively. However, at each treatment time, the reduction of populations of *L. innocua* was significantly lower ($p<0.05$) than that of *E. coli*. Also, no significant difference ($p>0.05$) was achieved among the three treatment time.

Interestingly, unlike the inactivation on the surface of TSA, the same duration of plasma treatment time resulted in different ($p<0.05$) reduction in the population between *E. coli* and *L. innocua*. A lower inactivation rate towards *L. innocua* indicates these bacteria attached on the surface of tomatoes became more resistant than that of *E. coli*. This can be partially attributed to the difference in cell characteristics between *E. coli* and *Listeria*. Cell characteristics are important factors for plasma species penetration and the inactivation efficacy of plasma treatment (Montie, IEEE Trans. plasma Sci. 28, 41-50, 2000; Otto et al., Food Eng. Rev. 3, 171-188, 2011). According to many studies, Gram-positive bacteria are in general more resistant than Gram-negative bacteria towards plasma treatment, as Gram-positive cells own thicker cell walls that can prevent reactive species from penetrating the membrane and oxidizing intracellular components (Ermolaeva et al., J. Med. Microbiol. 60, 75-83, 2011; Fröhling et al., Food Microbiol. 33, 24-29, 2012; Ziuzina et al., Food Microbiol. 42, 109-116, 2014). However, there has been also contradicting results showing that Gram-positive bacteria are less (Fan et al., J. Food Prot. 75, 1611-1618, 2012) or equally resistant (Klampfl et al., Appl. Environ. Microbiol. 78, 5077-5082, 2012; Kostov et al., Surf. Coatings Technol. 204, 2954-2959, 2010; Ölmez and Temur, LWT—Food Sci. Technol. 43, 964-970, 2010) towards plasma treatment. So far, no clear trend has been concluded about the differences of resistance towards plasma among cell types.

Another reason that might cause the inactivation variation towards *E. coli* and *Listeria* is the differences in the surface attachment of two bacteria. The numbers of cells attached on the surface of produce and the pattern of attachment have been shown to be different among bacteria, which was the reflection of the nature of the microorganisms' surface properties, the mechanisms, and the strengths of bacterial attachment (Takeuchi et al., J. Food Prot. 63, 1433-1437, 2000). *E. coli* and *Listeria* differ in attachment preference due to the differences in the bacterial surface hydrophobicity and the motility of the organisms. It was observed in the present study that the average initial attached population of *L. innocua* was significantly higher ($p<0.05$) than that of *E. coli*, which might be attributed to the different patterns of attachment between the two bacteria. This difference in initial attached population complicates the comparison of the sensitivity of the two bacteria, as a higher concentration of cells is generally more resistant to harsh environment by forming multi-layers or clumps that protect themselves from the harmful treatment (BermUdez-Aguirre et al., Food Control 34, 149-157, 2013; Deng et al., Appl. Phys. Lett. 87, 1-3, 2005). Therefore, a higher inactivation rate of the SDBD plasma towards *E. coli* than *L. innocua* might be due to the variation in cell characteristics, the pattern of attachment on tomato surface, and a lower initial attached population between the two bacteria.

Tomato and spinach represent different surface categories, providing different challenges for plasma decontamination. A higher inactivation efficacy is expected to achieve for bacteria inoculated on the smooth surface of tomatoes than leafy green. However, in the present study, the inactivation efficacy on tomato and spinach was not comparable since the setting of the SDBD devices for tomato and spinach were different. The circular electrodes used for spinach decontamination was supposed to show higher inactivation efficacy due to its closer distance to the external surface of food and better sealing quality that less reactive species will escape from the space around the food surface. On the contrary, the distance from the two-cone electrodes to tomato surface was longer so that the charged particles and the short-lived species might not be to able to affect the sample under treatment due to their short half-life and potential to recombine before reaching the sample (Laroussi and Leipold, Int. J. Mass Spectrom. 233, 81-86, 2004; Misra et al., J. Biosci. Bioeng. 118, 177-182, 2013). Thus, in the present study, the two settings of SDBD electrodes might have contributed to the different inactivation rates between bacteria attached to the surface of tomatoes and baby spinach leaves.

B. Effect of SDBD Plasma Treatment on the Quality Attributes of Fresh Produce (a) Assessment of Firmness, Color, and Visual Appearance Besides the microbial safety aspect, the quality of fresh produce is also important. Firmness, color, and visual appearance are critical quality attributes in the consumer acceptability of fresh produce. The firmness of spinach and tomatoes with or without plasma treatment at the end of the storage period (7 days) is shown in Table 2. The maximum force of penetration for untreated and plasma-treated baby spinach leaves was 113.72±25.05 g (control), 139.17±25.04 g (2 min), 105.22±36.01 g (5 min), and 104.74±44.34 g (10 min), respectively, while for tomato samples the values were 829.90±69.12 g (control), 867.54±58.82 g (2 min), 873.93±69.23 g (5 min), and 861.02±59.87 g (10 min), respectively. No notable change ($p>0.05$) in firmness was observed in either plasma-treated spinach or tomatoes, regardless of the plasma treatment time, indicating the SDBD plasma treatment did not cause significant physiological stress that leads to the change of tissue softening.

The color of spinach and tomatoes before and after plasma treatment, as well as over the storage period, was measured and represented by CIE L* a* b* values (Table 3). For baby spinach (Table 3), there was no significant difference ($p>0.05$) of L*, a*, or b* values between the treated and untreated samples over storage at refrigerated temperature. The overall color change, as indicated by the ΔE* value, increased over storage for both plasma-treated samples and controls. On the same day during storage, samples of longer plasma treatment time showed higher E* values. This result indicates a larger degree of color change caused by longer plasma treatment over storage. However, only on day-7, samples treated by plasma for 5 minutes or 10 minutes showed a significant ($p<0.05$) increased ΔE* value compared with other samples. Different from baby spinach, tomato samples did not show significant change ($p>0.05$) in L*, a*, b*, or ΔE* value after plasma treatment, regardless of the plasma treatment time and the day of storage (Table 4).

Figure 14A:
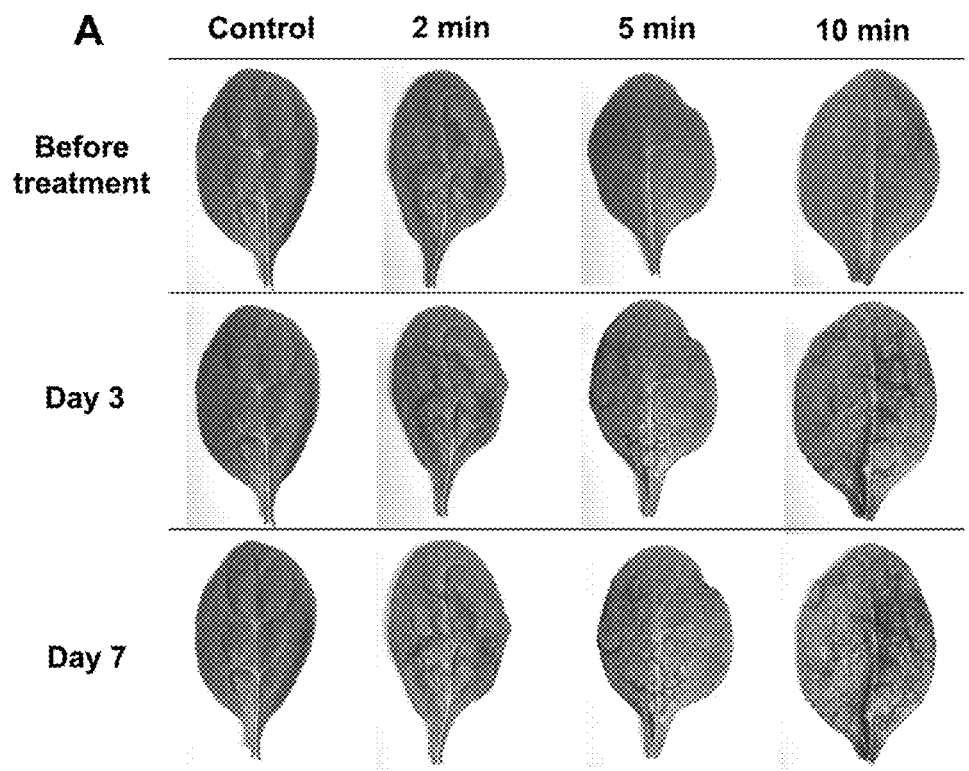
FIGS. 14A and 14B are a set of diagrams showing visual appearance of the control or SDBD plasma treated baby spinach leaves (FIG. 14A) or whole tomatoes (FIG. 14B) over storage for up to 7 days.
Figure 14B:
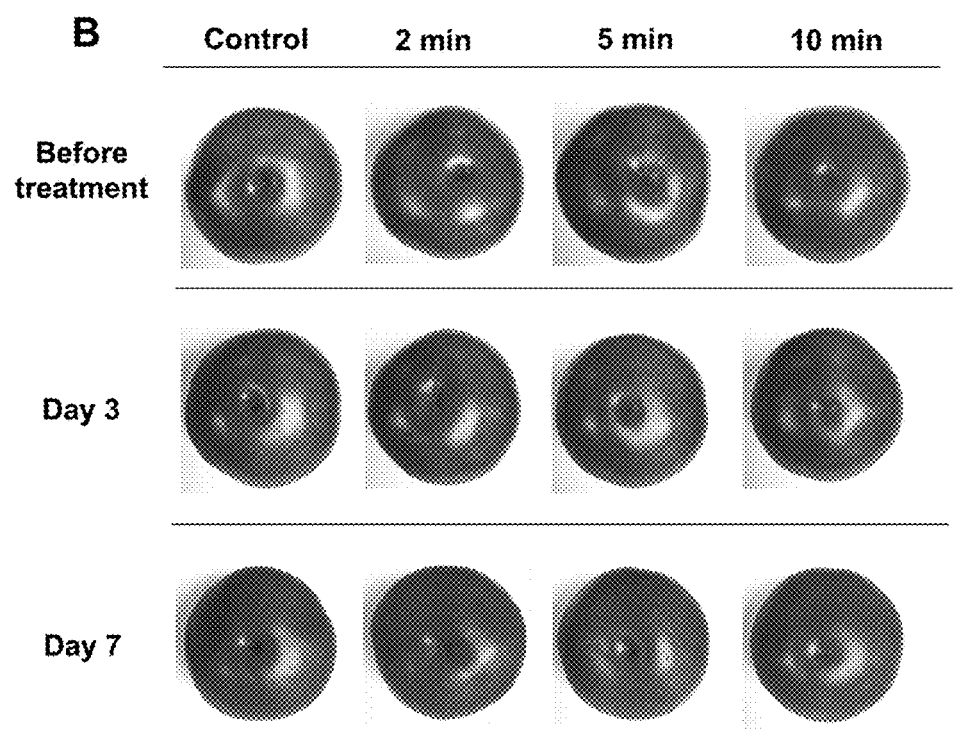

Visual observation of samples at the different days of storage (FIGS. 14A and 14B) validated the results of color measurement that spinach treated by plasma showed regional discoloration and signs of surface drying, with longer plasma exposure time showing the larger extent of appearance change. Over storage, the discoloration became more visible, and cracks started to show up on the surface of leaves treated by plasma for 5 minutes or 10 minutes. This visual change of spinach by plasma indicates the possible chemical reactions with the surface components, which might be the chemical species from plasma that promoted the disintegration of cell membranes by oxidation (Grzegorzewski et al., LWT—Food Sci. Technol. 44, 2285-2289, 2011). Different from spinach leaves, plasma-treated tomatoes over storage were not observed any visual difference in color or texture, probably because of the protection of wax cuticle of tomato surface and the longer treatment distance of the two-cone electrodes.

TABLE 2

Firmness (g) of baby spinach leaves or whole tomatoes of various treatment time by SDBD plasma at the end of the storage period (7 days). Mean ± SD. Means followed by the same letter in the same column are non-significant at $P < 0.05$ according to Tukey's HSD test.

| Plasma treatment time (min) | Firmness (g) | |
| --- | --- | --- |
| | Spinach | Tomato |
| 0 (control) | 114 ± 25$^a$ | 830 ± 69$^a$ |
| 2 | 139 ± 25$^a$ | 868 ± 50$^a$ |
| 5 | 105 ± 36$^a$ | 874 ± 69$^a$ |
| 10 | 105 ± 44$^a$ | 861 ± 60$^a$ |

TABLE 3

CIE L*-a*-b* values of baby spinach leaves of various treatment time by SDBD plasma over storage for 7 days. Mean ± SD. Means followed by the same letter in the same column are non-significant at $P < 0.05$ according to Tukey's HSD test.

| Storage duration | Plasma treatment time (min) | L* | a* | b* | ΔE* |
| --- | --- | --- | --- | --- | --- |
| Before treatment | 0 (control) | 44.39 ± 1.43$^a$ | −8.89 ± 0.94$^a$ | 20.78 ± 2.51$^a$ | |
| | 2 | 41.13 ± 3.62$^a$ | −8.55 ± 0.40$^a$ | 18.80 ± 2.09$^a$ | |
| | 5 | 43.49 ± 2.34$^a$ | −8.90 ± 0.32$^a$ | 21.89 ± 2.27$^a$ | |
| | 10 | 43.77 ± 2.86$^a$ | −9.73 ± 1.26$^a$ | 22.01 ± 3.33$^a$ | |
| Day 0 (immediately after treatment) | 0 (control) | 44.39 ± 1.43$^a$ | −8.89 ± 0.94$^a$ | 20.78 ± 2.51$^a$ | |
| | 2 | 40.14 ± 4.27$^a$ | −8.10 ± 0.31$^a$ | 18.80 ± 2.10$^a$ | 1.58 ± 0.31$^b$ |
| | 5 | 41.09 ± 2.34$^a$ | −8.90 ± 0.32$^a$ | 21.89 ± 2.27$^a$ | 2.56 ± 0.47$^{ab}$ |
| | 10 | 41.26 ± 3.82$^a$ | −9.31 ± 0.80$^a$ | 22.01 ± 3.33$^a$ | 2.39 ± 1.08$^{ab}$ |
| Day 3 | 0 (control) | 41.33 ± 1.44$^a$ | −9.40 ± 0.93$^a$ | 21.19 ± 2.50$^a$ | 3.69 ± 0.10$^{ab}$ |
| | 2 | 38.63 ± 4.48$^a$ | −8.60 ± 0.95$^a$ | 19.73 ± 3.12$^a$ | 3.43 ± 0.54$^{ab}$ |
| | 5 | 40.46 ± 3.51$^a$ | −8.64 ± 0.41$^a$ | 19.98 ± 1.64$^a$ | 3.98 ± 0.57$^{ab}$ |
| | 10 | 41.50 ± 5.23$^a$ | −9.23 ± 1.14$^a$ | 21.97 ± 2.71$^a$ | 4.48 ± 0.67$^{ab}$ |
| Day 7 | 0 (control) | 42.14 ± 1.71$^a$ | −9.47 ± 0.56$^a$ | 22.30 ± 2.40$^a$ | 3.55 ± 1.60$^{ab}$ |
| | 2 | 39.41 ± 2.41$^a$ | −9.42 ± 0.99$^a$ | 21.92 ± 2.62$^a$ | 4.41 ± 1.74$^{ab}$ |
| | 5 | 38.82 ± 3.66$^a$ | −8.71 ± 0.51$^a$ | 20.29 ± 1.85$^a$ | 5.20 ± 2.28$^a$ |
| | 10 | 42.05 ± 5.88$^a$ | −9.32 ± 0.62$^a$ | 22.49 ± 2.05$^a$ | 5.78 ± 1.77$^a$ |

TABLE 4

CIE L*-a*-b* values of whole tomatoes of various treatment time by SDBD plasma over storage for 7 days. Mean ± SD. Means followed by the same letter in the same column are non-significant at $P < 0.05$ according to Tukey's HSD test.

| Storage duration | Plasma treatment time (min) | L* | a* | b* | ΔE* |
| --- | --- | --- | --- | --- | --- |
| Before treatment | 0 (control) | 38.46 ± 2.17$^a$ | 26.49 ± 2.93$^a$ | 25.03 ± 5.57$^a$ | |
| | 2 | 37.26 ± 0.77$^a$ | 26.52 ± 3.89$^a$ | 25.68 ± 7.71$^a$ | |
| | 5 | 38.71 ± 5.52$^a$ | 25.72 ± 3.39$^a$ | 26.48 ± 5.72$^a$ | |
| | 10 | 36.27 ± 4.86$^a$ | 25.44 ± 2.73$^a$ | 24.80 ± 2.53$^a$ | |
| Day 0 (Immediately after treatment) | 0 (control) | 38.46 ± 2.17$^a$ | 26.49 ± 2.93$^a$ | 25.03 ± 5.57$^a$ | |
| | 2 | 38.07 ± 1.65$^a$ | 25.12 ± 2.69$^a$ | 24.97 ± 4.73$^a$ | 2.98 ± 0.77$^a$ |
| | 5 | 39.44 ± 5.80$^a$ | 23.67 ± 3.48$^a$ | 23.75 ± 3.04$^a$ | 2.86 ± 1.04$^a$ |
| | 10 | 36.66 ± 2.13$^a$ | 24.12 ± 1.69$^a$ | 22.29 ± 1.96$^a$ | 2.70 ± 0.26$^a$ |
| Day 3 | 0 (control) | 38.57 ± 0.47$^a$ | 26.41 ± 2.95$^a$ | 28.26 ± 7.55$^a$ | 2.89 ± 0.86$^a$ |
| | 2 | 35.37 ± 2.03$^a$ | 26.88 ± 3.28$^a$ | 28.34 ± 4.65$^a$ | 2.41 ± 0.34$^a$ |
| | 5 | 35.84 ± 6.02$^a$ | 27.31 ± 4.81$^a$ | 29.35 ± 2.01$^a$ | 2.52 ± 0.82$^a$ |
| | 10 | 32.30 ± 1.47$^a$ | 28.57 ± 2.87$^a$ | 29.44 ± 4.57$^a$ | 2.81 ± 1.42$^a$ |
| Day 7 | 0 (control) | 38.17 ± 1.12$^a$ | 27.02 ± 1.38$^a$ | 28.72 ± 4.00$^a$ | 2.39 ± 0.71$^a$ |
| | 2 | 37.23 ± 2.16$^a$ | 24.46 ± 3.38$^a$ | 28.28 ± 4.99$^a$ | 3.01 ± 1.01$^a$ |
| | 5 | 38.11 ± 5.37$^a$ | 23.96 ± 2.16$^a$ | 24.33 ± 3.51$^a$ | 3.39 ± 0.53$^a$ |
| | 10 | 35.85 ± 2.88$^a$ | 25.04 ± 3.32$^a$ | 22.62 ± 2.67$^a$ | 2.80 ± 0.82$^a$ |

(b) Weight Loss and pH Change

Figures 15A, 15B:
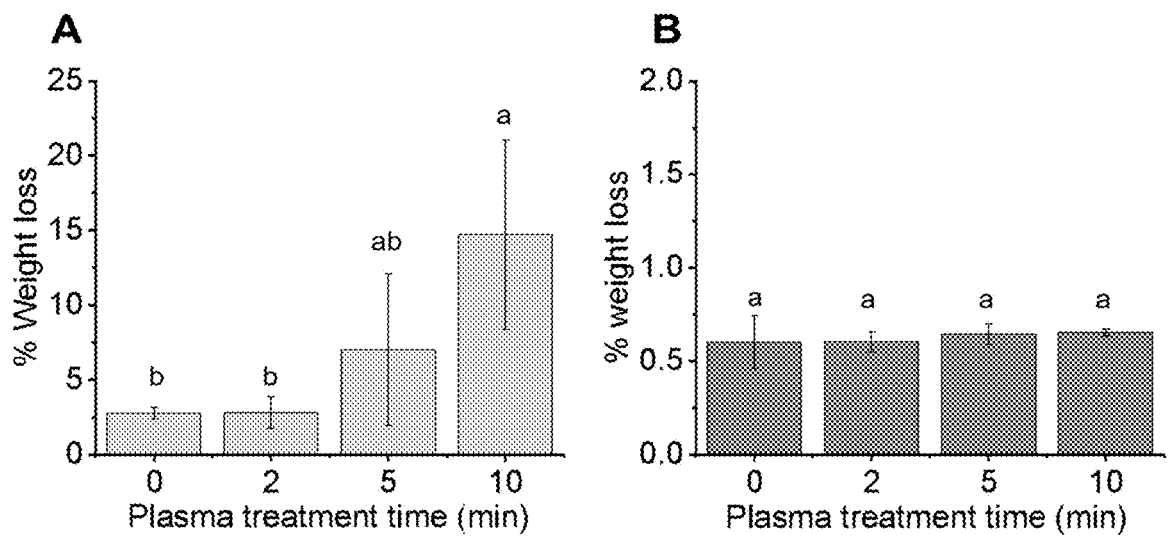
FIGS. 15A and 15B are a set of graphs showing weight loss (% of initial weight) of baby spinach leaves (FIG. 15A) or whole tomatoes (FIG. 15B) of various treatment time by SDBD plasma at the end of storage period (7 days). Mean±SD. Means followed by the same letter in the same column are non-significant at $P<0.05$ according to Tukey's HSD test.

The weight loss of samples of various plasma treatment time at the end of 7-days storage is shown in FIGS. 15A and 15B. Baby spinach displayed variable weight loss that samples treated by plasma for 5 minutes or 10 minutes lost 7.0±5.1% and 14.7±6.3% of their average original weights, respectively, and the weight loss of 10 minutes treatment was significantly higher (p<0.05) than that of the control. Spinach samples of 2 minute plasma treatment (2.8±0.4%) did not show significant (p>0.05) weight loss compared with control (2.8±1.1%) after storage (FIG. 15A). The higher rate of water loss from the spinach underwent for a longer plasma-treatment might be due to the cracks on the surface of the leaves after treatment, resulting in increased water evaporation and escape of gas from the tissues during respiration. The variation of surface modification among leaves probably contributed to the large standard deviation of the average weight loss. For tomatoes (FIG. 15B), the plasma-treated samples did not show significant (p>0.05) loss of weight, which is consistent with the visual observation. This might be attributed to the wax surface property of tomato that less oxidation and modification are likely to be made by plasma on tomato.

Figures 16, 16A:
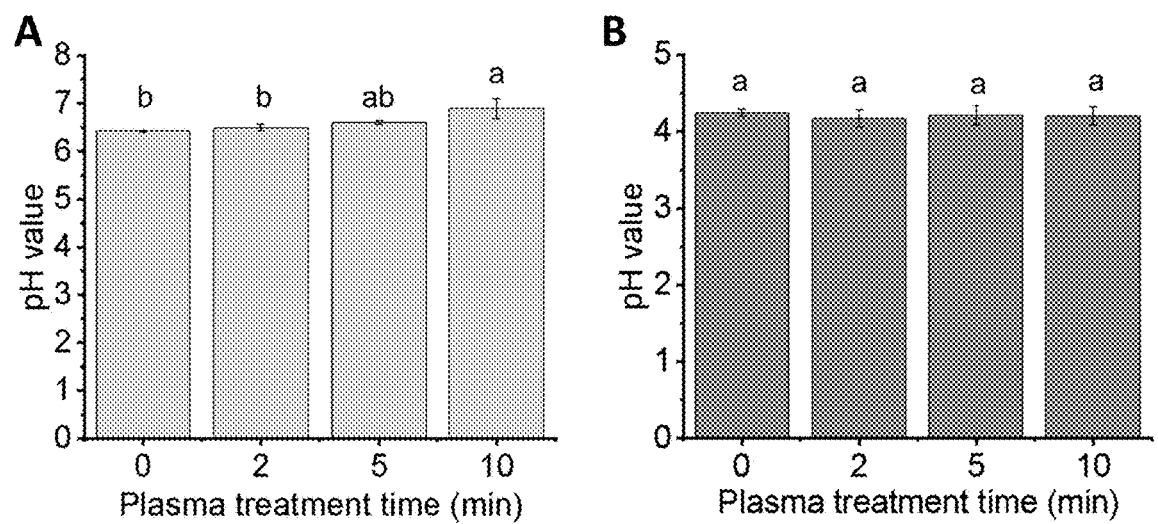

The pH values of control (untreated) and plasma-treated samples are shown in FIGS. 16A and 16B. After plasma treatment, the pH of spinach leaves became higher (FIG. 16A). Although the increase of pH value was slight, a significant increase (p<0.05) of pH after 10 minutes of treatment was noticed. On the contrary, no significant difference in pH among plasma-treated tomatoes and control was identified (FIG. 16B). The reason for the increase in the pH value of spinach after plasma treatment is not well known yet. So far, only limited information regarding the effect of plasma treatment on the pH of fresh produce and the discussion of the mechanisms of the changes has been reported. The change of pH, in this case, can be an indicator of chemical modification on the surface of leaves.

8. Fabric-Based Plasma Generators

This example describes the development of a plasma generating patch using fabric coated with silver nanowire for wound healing applications. The fabric-based plasma devices are simple in construction, highly flexible, and conformable on curvilinear surfaces, thus suitable for wearable applications. The devices use a surface dielectric barrier discharge (SDBD) methodology to create atmospheric plasma when electrically driven with oscillating peak-to-peak potentials of ±8.5 kV. The fabric-based devices produced surface plasmas containing a significant amount of reactive oxygen and nitrogen species (RONS) that are effective against microbes. The characterization of plasma generated from these devices showed the presence of reactive nitrogen species, a high level of ozone (4.5 ppm with 60 s of activation), a detectable level of UVC, and modest surface temperature (~50° C. after 90 s of activation). The fabric-based plasma devices deactivated 3- and 4-log of *Escherichia coli* cells with 1- and 3-minute treatments, respectively. The device gradually lost the plasma generation capability (40% reduction over 31 cycles).

The plasma exposure on a wounded mouse showed that the device could safely administer plasma during in vivo studies. These results show that the device is suitable for sanitation of wounds and contaminated surfaces with antibiotic-resistant bacteria. Besides, this work shows an envisioned plasma-patch for future wound healing applications. Overall, this work demonstrated the applicability of cold plasma in a flexible and wearable format, which may steer the current plasma medicine research towards wearable and personalized medicine.

The optimization of electrical parameters is crucial to generate uniform plasma on the edges of the electrode. Therefore, the optimal frequency of the fabric-based plasma devices in the air was investigated. To that end, a circular plasma device of 2.83-inch diameter was fabricated, having hexagonal tiling features of 4 mm sides and a spacing of 3 mm. The hexagonal tiling arrangement creates uniform electrical paths and maximum edges over a surface for plasma generation as this arrangement allows complete surface coverage with a minimum amount of total perimeter to cover a surface completely. The voltage was initially raised from ±2 kV to ±8.5 kV. Over ±8.5 kV, the device shorted as the barrier material failed. Then frequency was varied between 2.5 kHz and 500 Hz to identify the optimal frequency for the device size and shape. It was found 1.2-1.5 kHz as the optimal frequency range of alternating current at ±8.5 kV with plasma coverage over the whole device and maximum glow. The power consumption for this fabric-based plasma generator was ~30 W for RMS 6 kV at ~5 mA. The plasma generation on a fabric-based device in a curved state with a radius of curvature about 1.5 cm, indicating that the devices are very flexible and work efficiently under a bent condition.

9. Patch-Based Plasma Generators for Wound Healing Applications

The disclosed plasma applicator can be configured as a wearable format, such as a plasma patch (or a patch-based plasma generator), to treat skin wounds. A plasma patch may include three components: (1) Adhesive patch: it carries the device, sticks around the wound, and provides a physical barrier for the reactive species to escape; (2) Plasma generator: this component is the functional component of the patch. It connects to the power supply and produces plasma; (3) Dielectric separator: this component provides the necessary space between the wound and device surface. It provides (a) electrical insulation to the skin and wound and (b) necessary volume of air where dielectric discharge can create plasma. In one example, the patch plasma was mounted on biceps brachii of a mannequin. An essential assumption while fabricating these devices is that the device can function on different curvilinear surfaces on the body. To confirm this assumption, two glasses having different curvilinear surfaces with two-directional curvature simulating the wrist and biceps areas of an arm were used. The radius of curvature in two directions for the first glass is ~3 cm and 21.5 cm, while 4.25 cm and 9.5 cm for the second glass. It was found that the device could indeed conform to different curvilinear surfaces, and the volume of air entrapped between the glass and generator surface was enough to produce plasma throughout the device. It is important to note that the device cannot create plasma if any part of the plasma generating surface touches the glass. Thus, the results also suggest that the insulation was adequate to isolate the device from the glass surface showing the potential use as an active bandage.

What is claimed is:
1. A plasma applicator consisting of:
   a first substrate layer, a second substrate layer, and an adhesive layer,
   wherein the first substrate layer and the second substrate layer are comprised of a fibrous base layer and a metallic surface layer,

29 wherein the adhesive layer binds the fibrous base layer of the first substrate layer to the fibrous base layer of the second substrate layer, wherein the metallic surface layer of the first substrate layer and the metallic surface layer of the second substrate are exposed and configured to be placed in conductive contact with a high voltage source to generate dielectric barrier discharge (DBD)-based plasma comprising at least one of volume plasma and surface plasma upon exposure to the high voltage source, and wherein the high voltage source is configured to apply an alternating current (AC) input with a frequency of about 1 kHz to about 10 kHz to the plasma applicator and a peak-to-peak voltage (Vp-p) ranging from about ±0.5 kV to about ±5 kV.

2. The plasma applicator of claim 1, wherein the AC input has a voltage of about 1 kV to about 100 kV.

3. The plasma applicator of claim 1, wherein the DBD-based plasma is configured to generate ozone.

4. The plasma applicator of claim 1, wherein the first substrate layer comprises a plurality of hexagon-shaped apertures forming a honeycomb pattern.

5. A bandage for promoting wound healing, comprising the plasma applicator of claim 1 and a non-conductive spacer attached on a surface of the plasma applicator, the non-conductive spacer being adapted to be placed on skin tissue.

6. A device for disinfecting or sanitizing an object, comprising the plasma applicator of claim 1.

7. The device of claim 6, wherein the object comprises food or produce.

8. A self-sanitizing article, comprising the plasma applicator of claim 1.

9. A system for deodorizing an object, comprising the plasma applicator of claim 1.

10. A device for oxidizing an article, comprising the plasma applicator of claim 1.

11. A method of disinfecting or sanitizing a surface using a plasma applicator, wherein the plasma applicator consists of:
a first substrate layer, a second substrate layer, and an adhesive layer,
wherein the first substrate layer and the second substrate layer are comprised of a fibrous base layer and a metallic surface layer,
wherein the adhesive layer binds the fibrous base layer of the first substrate layer to the fibrous base layer of the second substrate layer,
wherein the metallic surface layer of the first substrate layer and the metallic surface layer of the second substrate are exposed and configured to be placed in conductive contact with a high voltage source to generate dielectric barrier discharge (DBD)-based plasma comprising at least one of volume plasma and surface plasma upon exposure to the high voltage source, and the method comprising:
placing the plasma applicator over the surface and thereby to cause the plasma applicator to directly contact the surface or to maintain a predetermined distance over the surface; and

30 applying an alternating current (AC) input from the high voltage source and keeping the plasma applicator over the surface for a predetermined amount of time, thereby causing the plasma applicator to generate DBD-based plasma that kills or inhibits growth of a microorganism or a virus on the surface.

12. The method of claim 11, wherein the step of applying comprises applying the AC input with a frequency of about 1 kHz to about 10 kHz to the plasma applicator and a peak-to-peak voltage (Vp-p) ranging from about ±0.5 kV to about ±5 kV.

13. The method of claim 11, wherein the step of applying comprises applying the AC input with a voltage of about 1 kV to about 100 kV to the plasma applicator.

14. A method of deodorizing an article using a plasma applicator, wherein the plasma applicator consists of:
a first substrate layer, a second substrate layer, and an adhesive layer,
wherein the first substrate layer and the second substrate layer are comprised of a fibrous base layer and a metallic surface layer,
wherein the adhesive layer binds the fibrous base layer of the first substrate layer to the fibrous base layer of the second substrate layer,
wherein the metallic surface layer of the first substrate layer and the metallic surface layer of the second substrate are exposed and configured to be placed in conductive contact with a high voltage source to generate dielectric barrier discharge (DBD)-based plasma comprising at least one of volume plasma and surface plasma upon exposure to the high voltage source, and the method comprising:
placing the plasma applicator over a surface of the article and thereby to cause the plasma applicator to directly contact the surface or to maintain a predetermined distance over the surface; and
applying an alternating current (AC) input from the high voltage source and keeping the plasma applicator over the surface for a predetermined amount of time, thereby causing the plasma applicator to generate DBD-based plasma that reduces odor from the article.

15. The method of claim 14, wherein the step of applying comprises applying to the plasma applicator the AC input with a frequency of about 1.0 kHz to about 3.5 kHz and a peak-to-peak voltage (Vp-p) ranging from about ±2.0 kV to about ±3.5 kV.

16. A method of oxidizing an object, comprising:
placing the plasma applicator of claim 1 over a surface of the article and thereby to cause the plasma applicator to directly contact the surface or to maintain a predetermined distance over the surface; and
applying an alternating current (AC) input from the high voltage source and keeping the plasma applicator over the surface for a predetermined amount of time, thereby causing the plasma applicator to generate DBD-based plasma that oxidizes the article.

17. The plasma applicator of claim 1, wherein the DBD-based plasma is configured to kill or inhibit growth of a microorganism or a virus on a surface or on an object.

* * * * *